(12) United States Patent
MacCoss et al.

(10) Patent No.: US 7,879,815 B2
(45) Date of Patent: Feb. 1, 2011

(54) NUCLEOSIDE ARYL PHOSPHORAMIDATES FOR THE TREATMENT OF RNA-DEPENDENT RNA VIRAL INFECTION

(75) Inventors: Malcolm MacCoss, Freehold, NJ (US); David B. Olsen, Lansdale, PA (US); Monica Donghi, Rome (IT); Cristina Gardelli, Rome (IT); Steven Harper, Rome (IT); Malte Meppen, Rome (IT); Frank Narjes, Rome (IT); Barbara Pacini, Rome (IT)

(73) Assignees: Merck Sharp & Dohme Corp., Rahway, NJ (US); Istituto di Ricerche di Biologia Molecolare P. Angeletti S.p.A., Pomezia, Rome (IT)

( * ) Notice: Subject to any disclaimer, the term of this patent is extended or adjusted under 35 U.S.C. 154(b) by 343 days.

(21) Appl. No.: 12/223,940

(22) PCT Filed: Feb. 12, 2007

(86) PCT No.: PCT/US2007/003862
§ 371 (c)(1),
(2), (4) Date: Aug. 13, 2008

(87) PCT Pub. No.: WO2007/095269
PCT Pub. Date: Aug. 23, 2007

(65) Prior Publication Data
US 2010/0234316 A1    Sep. 16, 2010

Related U.S. Application Data

(60) Provisional application No. 60/773,009, filed on Feb. 14, 2006, provisional application No. 60/832,832, filed on Jul. 24, 2006.

(51) Int. Cl.
*A01N 43/04* (2006.01)
*A61K 31/70* (2006.01)
(52) U.S. Cl. .................................... 514/49; 514/43
(58) Field of Classification Search ............ None
See application file for complete search history.

(56) References Cited

U.S. PATENT DOCUMENTS

| | | | |
|---|---|---|---|
| 6,312,662 B1 | 11/2001 | Erion et al. | |
| 6,914,054 B2 | 7/2005 | Sommadossi et al. | |
| 2004/0181051 A1 | 9/2004 | Storer et al. | |
| 2005/0009737 A1 | 1/2005 | Clark | |
| 2005/0009775 A1 | 1/2005 | Howes et al. | |
| 2007/0197463 A1 | 8/2007 | Chun et al. | |

FOREIGN PATENT DOCUMENTS

WO    WO 2006/063149 A1    6/2006

WO    WO 2006/121820 A1    11/2006

OTHER PUBLICATIONS

Bartenschlager, R. "Candidate Targets for Hepatitis C Virus-Specific Antiviral Therapy", Intervirology, 1997, vol. 40, pp. 378-393.
Crabb, C. "Hard-Won Advances Spark Excitement About Hepatitis C", Science, 2001, vol. 294, pp. 506-507.
Dymock, B. "Emerging therapies for hepatitis C virus infection", Emerging Drugs, 2001, vol. 6, pp. 13-42.
Dymock, B. et al. "Novel approaches to the treatment of hepatitis C virus infection", Antiviral Chemistry & Chemotherapy, 2000, vol. 11, pp. 79-96.
Eldrup, A. et al. "Structure-Activity Relationship of Purine Ribonucleosides for Inhibition of Hepatitis C Virus RNA-Dependent RNA Polymerase", J. Med. Chem., 2004, vol. 47, pp. 2283-2295.
Hoffmann, P. et al. "Recent patents on experimental therapy for hepatitis C virus infection (1999-2002)", Expert. Opin. Ther. Patents, 2003, vol. 13, pp. 1707-1723.
Ishi, K. et al. "Expression of Hepatitis C Virus NS5B Protein: Characterization if Its RNA Polymerase Activity and RNA Binding", Hepatology, 1999, vol. 29, pp. 1227-1235.
Lauer, G. et al. "Hepatitis C Virus Infection", New England Journal of Medicine, 2001, vol. 345, pp. 41-52.

(Continued)

*Primary Examiner*—Patrick T Lewis
(74) *Attorney, Agent, or Firm*—Kenneth R. Walton; Sheldon O. Heber; Philippe L. Durette

(57) ABSTRACT

The present invention provides nucleoside aryl phosphoramidates of structural formula (I) which are precursors to inhibitors of RNA-dependent RNA viral polymerase. These compounds are precursors to inhibitors of RNA-dependent RNA viral replication and are useful for the treatment of RNA-dependent RNA viral infection. They are particularly useful as precursors to inhibitors of hepatitis C virus (HCV) NS5B polymerase, as precursors to inhibitors of HCV replication, and/or for the treatment of hepatitis C infection. The invention also describes pharmaceutical compositions containing such nucleoside aryl phosphoramidates alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the nucleoside aryl phosphoramidates of the present invention.

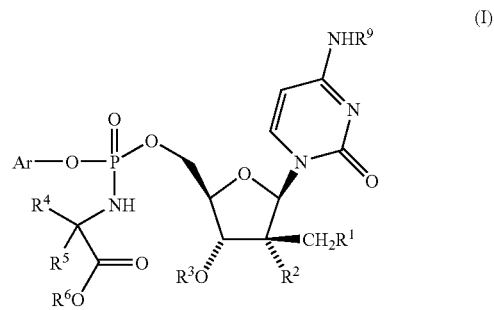

(I)

18 Claims, No Drawings

OTHER PUBLICATIONS

Lohmann, V. et al. "Biochemical and Kinetic Analyses of NS5B RNA-Dependent RNA Polymerase of the Hepatitis C Virus", Virology, 1998, vol. 249, pp. 108-118.

McGuigan, C. et al. "Application of Phosphoramidate Pronucleotide Technology to Abacavir Leads to a Significant Enhancement of Antiviral Potency", Journal of Medicinal Chemistry, 2005, vol. 48, pp. 3504-3515.

Moradpour, D. et al. "Current and evolving therapies for hepatitis C", European Journal of Gastroenterology & Hepatology, 1999, vol. 11, pp. 1199-1202.

Rosen, H. et al. "Hepatitis C virus: current understanding and prospects for future therapies", Molecular Medicine Today, 1999, vol. 5, pp. 393-399.

Siccardi, D. et al. Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers, The Journal of Pharmacology and Experimental Therapeutics, 2003, vol. 307, pp. 1112-1119.

Siddiqui, A. et al. "The Presence of Substituents on the Aryl Moiety of the Aryl Phosphoramidate Derivative of d4T Enhances Anti-HIV Efficacy in Cell Culture: A Structure-Activity Relationship", Journal of Medicinal Chemistry, 1999, vol. 42, pp. 393-399.

Takamatsu, S. et al. "Convenient Synthesis of Fluorinated Nucleosides with Perfluoroalkanesulfonyl Fluorides", Nucleosides, Nucleotides & Nucleic Acids, 2002, vol. 21, pp. 849-861.

Uchiyama, M. et al. "O'Selective Phosphorylation of Nucleotides without N-Protection", Journal of Organic Chemistry, 1993, vol. 58, pp. 373-379.

Walker, M. et al. "Promising candidates for the treatment of chronic hepatitis C", Expert Opin. Investig. Drugs, 2003, vol. 12, pp. 1269-1280.

NUCLEOSIDE ARYL PHOSPHORAMIDATES FOR THE TREATMENT OF RNA-DEPENDENT RNA VIRAL INFECTION

CROSS-REFERENCE TO RELATED APPLICATIONS

This application is the National Stage of International Application No. PCT/US2007/003862, filed on Feb. 12, 2007, which claims the benefit of U.S. Provisional Application No. 60/773,009 (filed Feb. 14, 2006) and U.S. Provisional Application No. 60/832,832 (filed Jul. 24, 2006), the disclosures of which are incorporated by reference herein in their entireties.

FIELD OF THE INVENTION

The present invention is concerned with nucleoside aryl phosphoramidates, their synthesis, and their use as precursors to inhibitors of RNA-dependent RNA viral polymerase. The compounds of the present invention are precursors to inhibitors of RNA-dependent RNA viral replication and are therefore useful for the treatment of RNA-dependent RNA viral infection. They are particularly useful as precursors to inhibitors of hepatitis C virus (HCV) NS5B polymerase, as precursors to inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science:* 506-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29: 1227-1235 (1999) and V. Lohmann, et al., "Biochemical and Kinetic Analyses of NS5B RNA-Dependent RNA Polymerase of the Hepatitis C Virus," *Virology*, 249: 108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs*, 12: 1269-1280 (2003) and in P. Hoffmann et al., "Recent patents on experimental therapy for hepatitis C virus infection (1999-2002)," *Expert Opin. Ther. Patents*," 13: 1707-1723 (2003). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47: 2283-2295 (2004). There is a continuing need for structurally diverse nucleoside derivatives as inhibitors of HCV polymerase as therapeutic approaches for HCV therapy.

It has now been found that nucleoside aryl phosphoramidates of the present invention are precursors to potent inhibitors of RNA-dependent RNA viral replication and in particular HCV replication. The phosphoramidates are converted in vivo into their nucleoside 5'-phosphate (nucleotide) derivatives which are converted into the corresponding nucleoside 5'-triphosphate derivatives which are inhibitors of RNA-dependent RNA viral polymerase and in particular HCV NS5B polymerase. The instant nucleoside phosphoramidates are useful to treat RNA-dependent RNA viral infection and in particular HCV infection.

It is therefore an object of the present invention to provide nucleoside aryl phosphoramidates which are useful as precursors to inhibitors of RNA-dependent RNA viral polymerase and in particular as precursors to inhibitors of HCV NS5B polymerase.

It is another object of the present invention to provide nucleoside aryl phosphoramidates which are useful as precursors to inhibitors of the replication of an RNA-dependent RNA virus and in particular as precursors to inhibitors of the replication of hepatitis C virus.

It is another object of the present invention to provide nucleoside aryl phosphoramidates which are useful in the treatment of RNA-dependent RNA viral infection and in particular in the treatment of HCV infection.

It is another object of the present invention to provide pharmaceutical compositions comprising the nucleoside aryl phosphoramidates of the present invention in association with a pharmaceutically acceptable carrier.

It is another object of the present invention to provide pharmaceutical compositions comprising the nucleoside aryl phosphoramidates of the present invention for use as precursors to inhibitors of RNA-dependent RNA viral polymerase and in particular as precursors to inhibitors of HCV NS5B polymerase.

It is another object of the present invention to provide pharmaceutical compositions comprising the nucleoside aryl phosphoramidates of the present invention for use as precursors to inhibitors of RNA-dependent RNA viral replication and in particular as precursors to inhibitors of HCV replication.

It is another object of the present invention to provide pharmaceutical compositions comprising the nucleoside aryl phosphoramidates of the present invention for use in the treatment of RNA-dependent RNA viral infection and in particular in the treatment of HCV infection.

It is another object of the present invention to provide pharmaceutical compositions comprising the nucleoside aryl phosphoramidates of the present invention in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide nucleoside aryl phosphoramidates and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the nucleoside aryl phosphoramidates of the present invention and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention relates to compounds of structural formula I of the indicated stereochemical configuration:

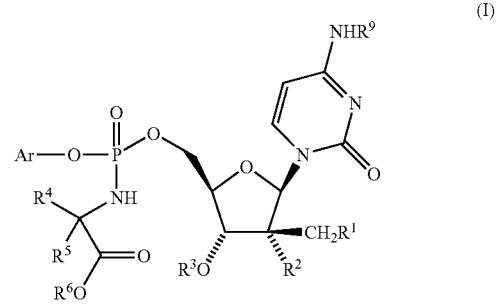

and pharmaceutically acceptable salts thereof; wherein n is 0, 1, or 2;

Ar is phenyl, naphthyl, pyridinyl, pyrimidinyl, pyrazinyl, pyridazinyl, indolyl, quinolinyl, or isoquinolinyl, wherein Ar is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^1$ is hydrogen or fluoro;

$R^2$ is fluoro, methoxy, or $OR^{10}$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

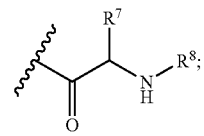

$R^{10}$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

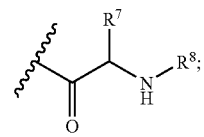

or $R^3$ and $R^{10}$ together with the oxygen atoms to which they are attached form a five-membered cyclic carbonate;

$R^4$ is hydrogen, $C_{1-5}$ alkyl, phenyl, or benzyl;
  wherein alkyl is optionally substituted with one substituent selected from the group consisting of fluorine, hydroxy, methoxy, amino, carboxy, carbamoyl, guanidine, mercapto, methylthio, 1H-imidazolyl, and 1H-indol-3-yl;
  and wherein phenyl and benzyl are optionally substituted with one to two substituents independently selected from the group consisting of halogen, hydroxy, and methoxy;

$R^5$ is hydrogen or methyl;

or $R^4$ and $R^5$ together with the carbon atom to which they attached form a 3- to 6-membered aliphatic spirocyclic ring system;

$R^6$ is hydrogen, $C_{1-16}$ alkyl, $C_{2-20}$ alkenyl, $(CH_2)_n C_{3-6}$ cycloalkyl, phenyl, benzyl, or adamantyl;
  wherein alkyl, alkenyl, cycloalkyl, and adamantyl are optionally substituted with one to three substituents independently selected from halogen, hydroxy, carboxy, $C_{1-4}$ alkoxy; and wherein phenyl and benzyl are optionally substituted with one to three substituents independently selected from halogen, hydroxy, cyano, $C_{1-4}$ alkoxy, trifluoromethyl, and trifluoromethoxy;

$R^7$ is hydrogen, $C_{1-5}$ alkyl, or phenyl $C_{0-2}$ alkyl;

$R^8$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl; and $R^9$ is hydrogen, $C_{1-8}$ alkylcarbonyl, or $C_{1-8}$ alkyloxycarbonyl.

The compounds of formula I are useful as precursors to inhibitors of RNA-dependent RNA viral polymerase and in particular of HCV NS5B polymerase. They are also precursors to inhibitors of RNA-dependent RNA viral replication and in particular of HCV replication and are useful for the treatment of RNA-dependent RNA viral infection and in particular for the treatment of HCV infection.

Without limitation as to their mechanism of action, the aryl phosphoramidates of the present invention act as precursors of the corresponding nucleoside 5'-monophosphates. Endogenous kinase enzymes convert the 5'-monophosphates into their 5'-triphosphate derivatives which are the inhibitors of the RNA-dependent RNA viral polymerase. Thus, the aryl phosphoramidates may provide for more efficient target cell penetration than the nucleoside itself, may be less susceptible to metabolic degradation, and may have the ability to target a specific tissue, such as the liver, resulting in a wider therapeutic index allowing for lowering the overall dose of the antiviral agent.

Also encompassed within the present invention are pharmaceutical compositions containing the compounds alone or in combination with other agents active against RNA-dependent RNA virus and in particular against HCV as well as methods for the inhibition of RNA-dependent RNA viral replication and for the treatment of RNA-dependent RNA viral infection.

DETAILED DESCRIPTION OF THE INVENTION

The present invention relates to compounds of structural formula I of the indicated stereochemical configuration:

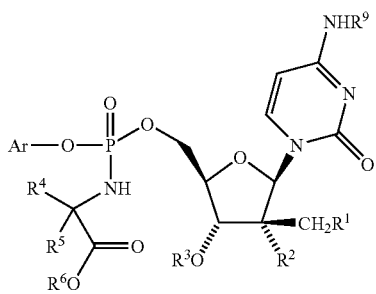

(I)

and pharmaceutically acceptable salts thereof; wherein
n is 0, 1, or 2;
Ar is phenyl, naphthyl, pyridinyl, pyrimidinyl, pyrazinyl, pyridazinyl, indolyl, quinolinyl, or isoquinolinyl, wherein Ar is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^1$ is hydrogen or fluoro;
$R^2$ is fluoro, methoxy, or $OR^{10}$;
$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

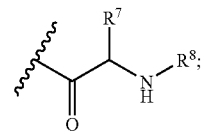

$R^{10}$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

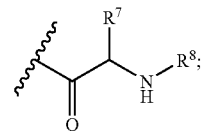

or $R^3$ and $R^{10}$ together with the oxygen atoms to which they are attached form a five-membered cyclic carbonate;

$R^4$ is hydrogen, $C_{1-5}$ alkyl, phenyl, or benzyl;
  wherein alkyl is optionally substituted with one substituent selected from the group consisting of fluorine, hydroxy, methoxy, amino, carboxy, carbamoyl, guanidino, mercapto, methylthio, 1H-imidazolyl, and 1H-indol-3-yl; and wherein phenyl and benzyl are optionally substituted with one to two substituents independently selected from the group consisting of halogen, hydroxy, and methoxy;

$R^5$ is hydrogen or methyl;
or $R^4$ and $R^5$ together with the carbon atom to which they attached form a 3- to 6-membered aliphatic spirocyclic ring system;

$R^6$ is hydrogen, $C_{1-16}$ alkyl, $C_{2-20}$ alkenyl, $(CH_2)_n C_{3-6}$ cycloalkyl, phenyl, benzyl, or adamantyl;
  wherein alkyl, alkenyl, cycloalkyl, and adamantyl are optionally substituted with one to three substituents independently selected from halogen, hydroxy, carboxy, $C_{1-4}$ alkoxy; and wherein phenyl and benzyl are optionally substituted with one to three substituents independently selected from halogen, hydroxy, cyano, $C_{1-4}$ alkoxy, trifluoromethyl, and trifluoromethoxy;

$R^7$ is hydrogen, $C_{1-5}$ alkyl, or phenyl $C_{0-2}$ alkyl;

$R^8$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl; and $R^9$ is hydrogen, $C_{1-8}$ alkylcarbonyl, or $C_{1-8}$ alkyloxycarbonyl.

The compounds of formula I are useful as precursors to inhibitors of RNA-dependent RNA viral polymerase. They are also precursors to inhibitors of RNA-dependent RNA viral replication and are useful for the treatment of RNA-dependent RNA viral infection.

In one embodiment of the compounds of the present invention, $R^1$ is hydrogen or fluoro, $R^2$ is hydroxy, and $R^3$ is hydrogen. In a class of this embodiment, $R^1$ is hydrogen.

In a second embodiment of the compounds of the present invention, $R^1$ is hydrogen or fluoro, $R^2$ is fluoro, and $R^3$ is hydrogen. In a class of this embodiment, $R^1$ is hydrogen.

In a third embodiment of the compounds of the present invention, Ar is phenyl optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl. In a class of this embodiment, Ar is phenyl substituted with three to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl. In a subclass of this class, Ar is phenyl substituted with three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, alkylcarbonyl, $C_{1-4}$ alkylcarbonyloxy, and $C_{1-4}$ alkyloxycarbonyl. In another class of this third embodiment, Ar is unsubstituted phenyl.

In a fourth embodiment of the compounds of the present invention, Ar is unsubstituted 1-naphthyl.

In a fifth embodiment of the compounds of the present invention, Ar is indolyl. In a class of this embodiment, Ar is 1H-indol-5-yl.

In a sixth embodiment of the compounds of the present invention, $R^5$ is hydrogen and $R^4$ is selected from the group consisting of hydrogen, methyl, ethyl, n-propyl, isopropyl, isobutyl, 2-methyl-1-propyl, hydroxymethyl, fluoromethyl, mercaptomethyl, carboxymethyl, carbamoylmethyl, 1-hydroxyethyl, 2-carboxyethyl, 2-carbamoylethyl, 2-methylthioethyl, 4-amino-1-butyl, 3-amino-1-propyl, 3-guanidino-1-propyl, 1H-imidazol-4-ylmethyl, phenyl, benzyl, 4-hydroxybenzyl, and 1H-indol-3-ylmethyl. In a class of this embodiment, $R^4$ is methyl or benzyl. In a subclass of this class, $R^4$ is methyl.

In a seventh embodiment of the compounds of the present invention, $R^6$ is $C_{1-8}$ alkyl, cyclohexyl, or cyclopentyl. In a class of this embodiment, $R^6$ is ethyl or butyl. In a another class of this embodiment, Ar is indolyl.

In an eighth embodiment of the compounds of the present invention, $R^6$ is $C_{7-16}$ alkyl. In a class of this embodiment, $R^6$ is $C_{8-12}$ alkyl. In a subclass of this class, $R^6$ is $C_8$ alkyl. In a subclass of this subclass, $R^6$ is 2-n-propyl-pent-1-yl.

In a ninth embodiment of the compounds of the present invention, Ar is phenyl or indolyl each of which is optionally substituted with one to three substituents selected from halogen and $C_{1-4}$ alkyl; $R^4$ is methyl; $R^6$ is ethyl or butyl; and $R^5$ is hydrogen. In a class of this embodiment, Ar is indolyl.

In a tenth embodiment of the compounds of the present invention, $R^4$ and $R^5$ are both methyl.

In an eleventh embodiment of the compounds of the present invention, Ar is unsubstituted phenyl and $R^6$ is $C_8$ alkyl. In a class of this embodiment, $R^6$ is 2-n-propyl-pent-1-yl.

Illustrative but nonlimiting examples of compounds of the present invention of structural formula I which are useful as precursors to inhibitors of RNA-dependent RNA viral polymerase are the following:

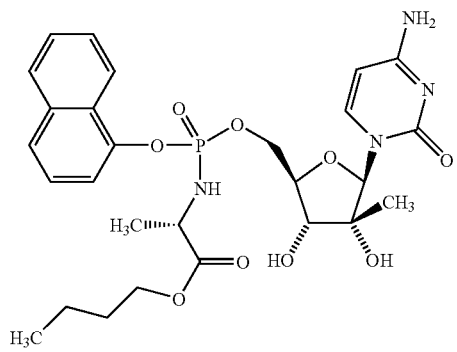

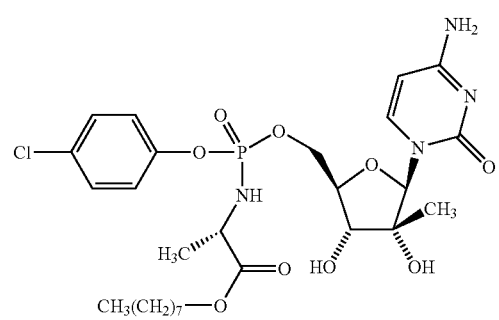

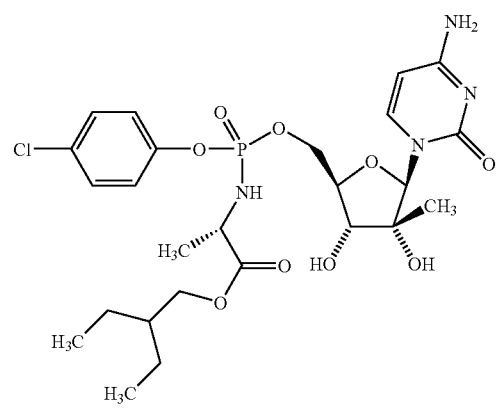

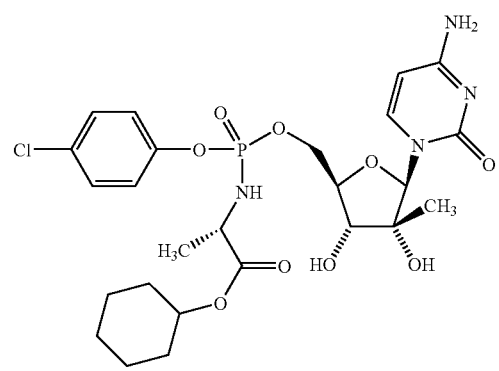

-continued

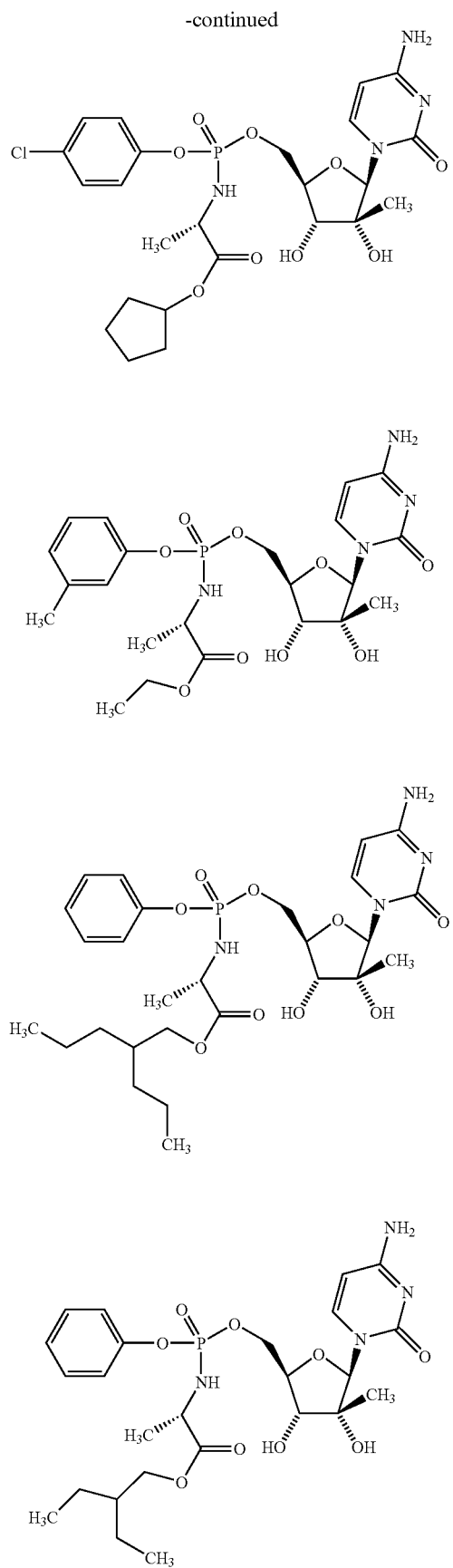
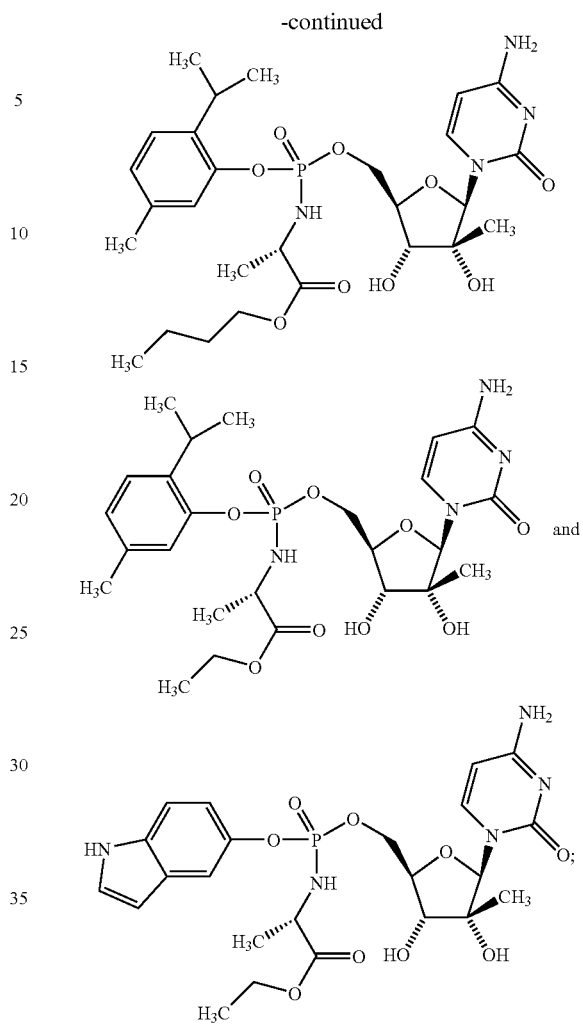

and pharmaceutically acceptable salts thereof.

In one embodiment of the present invention, the nucleoside aryl phosphoramidates of the present invention are useful as precursors to inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picornaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect of the present invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picornaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a second embodiment of this aspect of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this class, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a third embodiment of this aspect of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "naphthyl" encompasses both 1-naphthyl (α-naphthyl) and 2-naphthyl (β-naphthyl).

The term "adamantyl" encompasses both 1-adamantyl and 2-adamantyl.

By the term "optionally substituted benzyl" is meant —CH$_2$Phenyl wherein the phenyl moiety is optionally substituted.

The term "alkenyl" shall mean straight or branched chain alkenes of two to twenty total carbon atoms, or any number within this range (e.g., ethenyl, propenyl, butenyl, pentenyl, oleyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid or carbamic acid group present in a compound of the present invention having the number of carbon atoms specified (e.g., $C_{1-8}$ alkyloxycarbonyl), or any number within this range [i.e., methyloxycarbonyl (MeOCO—), ethyloxycarbonyl, or butyloxycarbonyl].

The term "alkylcarbonyl" refers to straight or branched chain alkyl acyl group of the specified number of carbon atoms (e.g., $C_{1-8}$ alkylcarbonyl), or any number within this range [i.e., methyloxycarbonyl (MeOCO—), ethyloxycarbonyl, or butyloxycarbonyl].

The term "halogen" is intended to include the halogen atoms fluorine, chlorine, bromine and iodine.

The term "phosphoryl" refers to —P(O)(OH)$_2$—.

The term "diphosphoryl" refers to the radical having the structure:

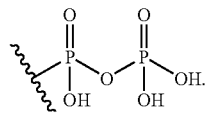

The term "triphosphoryl" refers to the radical having the structure:

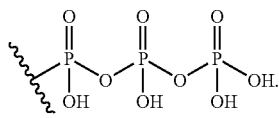

The term "five-membered cyclic carbonate ring" denotes the following ring system formed at the C-2 and C-3 positions of the furanose ring of the nucleoside by acylating the C-2 and C-3 hydroxyls with a carbonylating reagent, such as phosgene and 1,1'-carbonyldiimidazole:

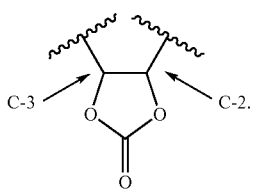

When $R^7$ in the amino acyl residue embodiment of $R^3$ and $R^{10}$ is a substituent other than hydrogen in the formula

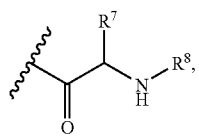

the amino acyl residue contains an asymmetric center and is intended to include the individual R- and S-stereoisomers as well as RS-diastereoisomeric mixtures. In one embodiment, the stereochemistry at the stereogenic carbon corresponds to that of an S-amino acid, that is, the naturally occurring alpha-amino acid stereochemistry, as depicted in the formula:

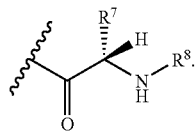

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "5'-triphosphate" refers to a triphosphoric acid ester derivative of the 5'-hydroxyl group of a nucleoside compound of the present invention having the following general structural formula II:

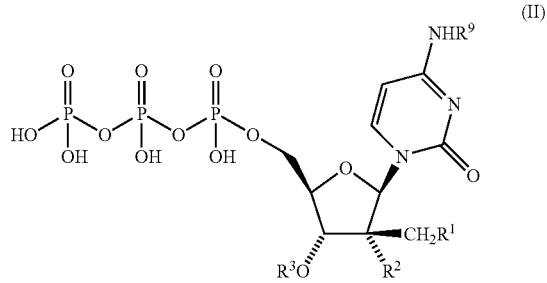

wherein $R^1$, $R^2$, $R^3$, and $R^9$ are as defined above.

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, nitazoxanide, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630; WO 99/07733, WO 99/07734, WO 99/38888, WO 99/50230, WO 99/64442, WO 00/09543, WO 00/59929, GB-2337262, WO 02/18369, WO 02/08244, WO 02/48116, WO 02/48172, WO 05/037214, and U.S. Pat. No. 6,323,180. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13-42 (2001). Specific HCV NS3 protease inhibitors combinable with the compounds of the present invention include BILN2061, VX-950, SCH6, SCH7, and SCH-503034.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754-1759 (1997); M. S. Wolfe, et al., *Tetrahedron Lett.*, 36: 7611-7614 (1995); U.S. Pat. No. 3,480, 613 (Nov. 25, 1969); U.S. Pat. No. 6,777,395 (Aug. 17, 2004); U.S. Pat. No. 6,914,054 (Jul. 5, 2005); International Publication Numbers WO 01/90121 (29 Nov. 2001); WO 01/92282 (6 Dec. 2001); WO 02/32920 (25 Apr. 2002); WO 02/057287 (25 Jul. 2002); WO 02/057425 (25 Jul. 2002); WO 04/002422 (8 Jan. 2004); WO 04/002999 (8 Jan. 2004); WO 04/003000 (8 Jan. 2004); WO 04/002422 (8 Jan. 2004); US Patent Application Publications 2005/0107312; US 2005/0090463; US 2004/0147464; and US 2004/0063658; the contents of each of which are incorporated by reference in their entirety. Such 2'-C-branched ribonucleosides include, but are not limited to, 2'-C-methylcytidine, 2'-fluoro-2'-C-methylcytidine 2'-C-methyluridine, 2'-C-methyladenosine, 2'-C-methylguanosine, and 9-(2-C-methyl-β-D-ribofuranosyl)-2,6-diaminopurine; the corresponding amino acid esters of the furanose C-2', C-3', and C-5' hydroxyls (such as 3'-O-(L-valyl)-2'-C-methylcytidine dihydrochloride, also referred to as valopicitabine dihydrochloride or NM-283 and 3'-O-(L-valyl)-2'-fluoro-2'-C-methylcytidine), and the corresponding optionally substituted cyclic 1,3-propanediol esters of their 5'-phosphate derivatives.

The compounds of the present invention may also be combined for the treatment of HCV infection with other nucleosides having anti-HCV properties, such as those disclosed in U.S. Pat. No. 6,864,244 (Mar. 8, 2005); WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003); US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004).

In one embodiment, nucleoside HCV NS5B polymerase inhibitors that may be combined with the nucleoside derivatives of the present invention are selected from the following compounds: 4'-azido-cytidine; 4-amino-7-(2-C-methyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C,2-O-dimethyl-β-D-ribofuranosyl)-7H-pyrrolo[2,3-d] pyrimidine; and pharmaceutically acceptable salts and prodrugs thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S P A.; WO 02/20497 (3 Mar. 2002); WO 2005/016927 (in particular JTK003), assigned to Japan Tobacco, Inc.; the contents of each of which are incorporated herein by reference in their entirety; and HCV-796 (Viropharma Inc.).

In one embodiment, non-nucleoside HCV NS5B polymerase inhibitors that may be combined with the nucleoside derivatives of the present invention are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5] benzodiazocine-11-carboxylic acid; 14-cyclohexyl-6-[2-(dimethylamino)ethyl]-3-methoxy-5,6,7,8-tetrahydroindolo [2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl] amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5] benzoxazocin-7-yl)-N,N-dimethylethane-1,2-diaminium bis (trifluoroacetate); 14-cyclohexyl-7,8-dihydro-6H-indolo[1, 2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5] benzodiazocine-11-carboxylic acid; 14-cyclohexyl-6-[2-(diethylamino)ethyl]-7-oxo-5,6,7,8-tetrahydroindolo[2,1-a] [2,5]benzodiazocine-11-carboxylic acid; 14-cyclohexyl-6-(1-methylpiperidin-4-yl)-7-oxo-5,6,7,8-tetrahydroindolo[2, 1-a][2,5]benzodiazocine-11-carboxylic acid; 14-cyclohexyl- N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

By "pharmaceutically acceptable" is meant that the carrier, diluent, or excipient must be compatible with the other ingredients of the formulation and not deleterious to the recipient thereof.

Also included within the present invention are pharmaceutical compositions comprising the nucleoside aryl phosphoramidates of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of the present invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics, and Therapeutic Potential," *Ann. Rep. Med. Chem.*, 35: 201-210 (2000).

Another aspect of the present invention provides for the use of the nucleoside aryl phosphoramidates and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the nucleoside aryl phosphoramidates and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereoisomeric mixtures and individual diastereoisomers. When $R^5$ is hydrogen and $R^4$ in the amino acyl residue attached to the phosphorus atom in structural formula I is a substituent other than hydrogen in the formula

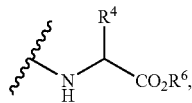

the amino acid residue contains an asymmetric center and is intended to include the individual R- and S-stereoisomers as well as RS-stereoisomeric mixtures. In one embodiment, the stereochemistry at the stereogenic carbon corresponds to that of an S-amino acid, that is, the naturally occurring alpha-amino acid stereochemistry, as depicted in the formula:

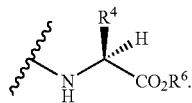

The tetrasubstituted phosphorus in compounds of structural formula I constitutes another asymmetric center, and the compounds of the present invention are intended to encompass both stereochemical configurations at the phosphorus atom.

The present invention is meant to comprehend nucleoside aryl phosphoramidates having the β-D stereochemical configuration for the five-membered furanose ring as depicted in the structural formula below, that is, nucleoside aryl phosphoramidates in which the substituents at C-1 and C-4 of the five-membered furanose ring have the β-stereochemical configuration ("up" orientation as denoted by a bold line).

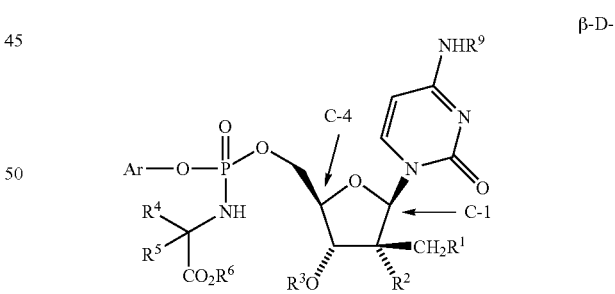

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formula I. Example of keto-enol tautomers which are intended to be encompassed within the compounds of the present invention are illustrated below:

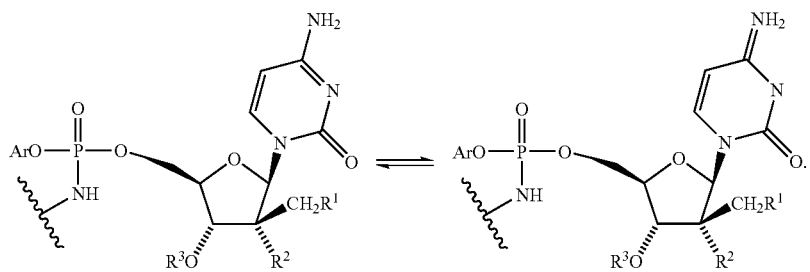

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate; maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or hydroxyl group being present in the compounds of the present invention, pharmaceutically acceptable prodrug esters of carboxylic acid derivatives, such as methyl, ethyl, or pivaloyloxymethyl esters or prodrug acyl derivatives of the ribose C-2', C-3', and C-5' hydroxyls, such as O-acetyl, O-pivaloyl, O-benzoyl and O-aminoacyl, can be employed. Included are those esters and acyl groups known in the art for modifying the bioavailability, tissue distribution, solubility, and hydrolysis characteristics for use as sustained-release or prodrug formulations. The contemplated derivatives are readily convertible in vivo into the required compound. Thus, in the methods of treatment of the present invention, the terms "administering" and "administration" is meant to encompass the treatment of the viral infections described with a compound specifically disclosed or with a compound which may not be specifically disclosed, but which converts to the specified compound in vivo after administration to the mammal, including a human patient. Conventional procedures for the selection and preparation of suitable prodrug derivatives are described, for example, in "Design of Prodrugs," ed. H. Bundgaard, Elsevier, 1985, which is incorporated by reference herein in its entirety.

Preparation of the Nucleoside Aryl Phosphoramidates of the Invention:

2'-C-Methylcytidine was prepared as described in the literature by C. Pierra et al., *Nucleosides, Nucleotides and Nucleic Acids*, 24: 767 (2005) or J. A. Piccirilli et al., *J. Org. Chem.*, 64: 747 (1999). 2'-Deoxy-2'-fluoro-2'-C-methylcytidine is prepared as described in *J. Med. Chem.*, 48: 5504-5508 (2005). The aryl phosphorochloridates for the phosphorylation reactions were prepared according to the methods described in U.S. Pat. No. 6,455,513, the contents of which are incorporated by reference herein in their entirety. The phosphorylation reactions to generate the aryl phosphoroamidates of the present invention were carried out following the methods described in U.S. Pat. No. 6,455,513 and C. McGuigan, et al., *J. Med. Chem.*, 36: 1048 (1993). For example, phenol or 1-naphthol was reacted with phosphorus oxychloride which was followed by coupling with different amino acid salts to give phenoxy or 1-naphthyloxy phosphorochloridates which were generally purified by flash chromatography and then coupled with the nucleoside in the presence of a suitable base, such as t-butylmagnesium chloride (see M. Uchiyama et al. *J. Org. Chem.*, 58: 373 (1993) and Scheme 1).

General Procedures:

All solvents were obtained from commercial sources and were used without further purification. Reactions were carried out under an atmosphere of nitrogen in oven dried (110° C.) glassware. Organic extracts were dried over sodium sulfate ($Na_2SO_4$), and were concentrated (after filtration of the drying agent) on rotary evaporators operating under reduced pressure. Flash chromatography was carried out on silica gel following published procedures (W. C. Still et al., J. Org. Chem., 43: 2923 (1978)) or on commercial flash chromatography systems (Biotage corporation and Jones Flashmaster II) utilising pre-packed columns.

Reagents were usually obtained directly from commercial suppliers (and used as supplied) or are readily accessible using routine synthetic steps that are either reported in the scientific literature or are known to those skilled in the art.

$^1$H and $^{31}$P NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a Perkin Elmer API 100, or Waters MicroMass ZQ, operating in negative (ES$^-$) or positive (ES$^+$) ionization mode and results are reported as the ratio of mass over charge (m/z) for the parent ion only. Preparative scale HPLC separations were carried out on a Waters 2525 pump, equipped with a 2487 dual absorbance detector, on a TSP Spectra system P4000 equipped with a UV1000 absorption module or on a automated, mass-triggered Waters Micromass system incorporating a 2525 pump module, a Micromass ZMD detector and a 2525 collection module. Compounds were eluted with linear gradients of water and MeCN both containing 0.1% trifluoroacetic acid or formic acid using flow rates between 10 and 40 mL/min. Symmetry C18 columns (7 μM, 19×300 mm) were used as stationary phase.

The following abbreviations are used in the examples, the schemes and the tables: aq.: aqueous; Ar: aryl; atm: atmosphere; $CCl_4$: carbon tetrachloride; DCM: dichloromethane; DMF: N,N-dimethylformamide; DMSO: dimethylsulfoxide; eq.: equivalent(s); $Et_3N$: triethylamine; EtOAc: ethyl acetate; $Et_2O$: diethyl ether; h: hour(s); Me: methyl; MeCN: acetonitrile; MeOH: methanol; min: minutes; MS: mass spectrum; N,N-DMA: N,N,-dimethylacetamide; PE: petroleum ether; Py: pyridine; quant.: quantitative; RP-HPLC: reversed phase high-performance liquid chromatography; RT: room temperature; sec: second(s); TFA: trifluoroacetic acid; and THF: tetrahydrofuran.

The Examples below provide illustrations of the conditions used for the preparation of the compounds of the present invention. These Examples are not intended to be limitations on the scope of the instant invention in any way, and they should not be so construed. Those skilled in the art of nucleoside and nucleotide synthesis will appreciate that known variations of the conditions and processes of the following preparative procedures can be used to prepare these and other compounds of the present invention. All temperatures are degrees Celsius unless otherwise noted.

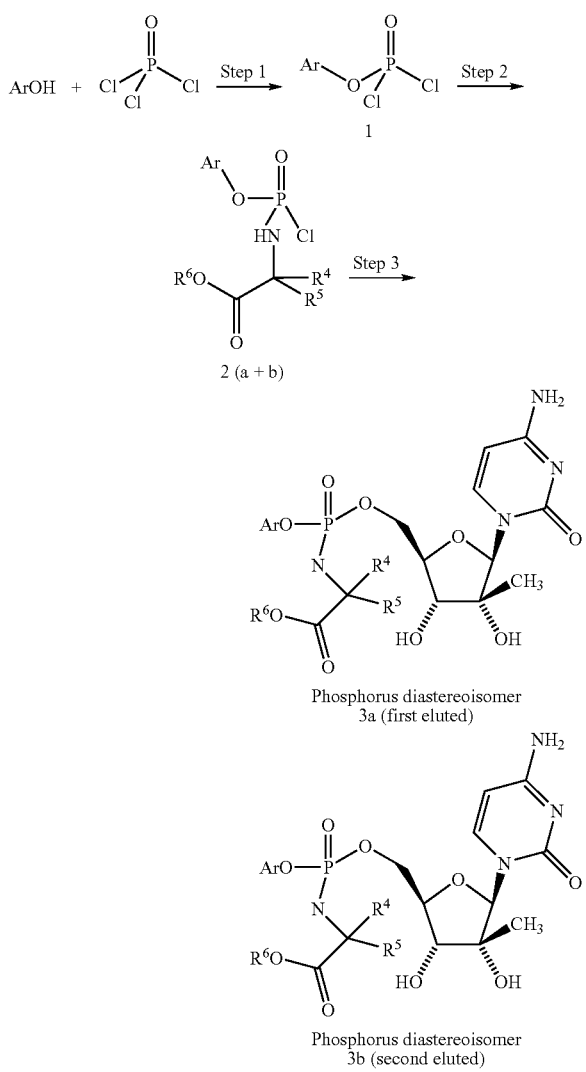

SCHEME 1

Phosphorus diastereoisomer
3a (first eluted)

Phosphorus diastereoisomer
3b (second eluted)

EXAMPLE 1

5'-O-[[[(1S)-2-n-butoxy-1-methyl-2-oxoethyl]amino](1-naphthalenyloxy)phosphinyl]-2'-C-methylcytidine Step 1: 1-Naphthyl dichlorophosphate

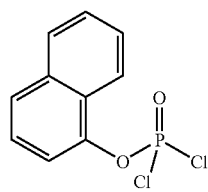

To 1-naphthol in $Et_2O$ (0.23 M) was added phosphorus oxychloride (1.0 eq.) and the solution was cooled to −78° C. Neat $Et_3N$ (1.0 eq) was added and the resulting solution was left to warm to RT overnight. The white slurry was filtered under an inert atmosphere and all volatiles were removed to yield the title compound as a colorless liquid that was used without further purification in the next step. $^{31}$P NMR (400 MHz, CDCl$_3$): δ 3.93 ppm.

Step 2: n-Butyl N-[chloro(1-naphthyloxy)phosphoryl]-L-alaninate

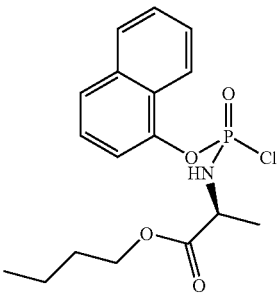

To 1-naphthyl dichlorophosphate in DCM (0.086 M) was added (2S)-1-butoxy-1-oxopropan-2-aminium chloride (1.0 eq.). After cooling to −78° C., neat Et$_3$N (2.0 eq.) was added and the reaction was left to warm to RT overnight. All volatiles were removed and the resulting white solid was washed with Et$_2$O, filtered and evaporated in vacuo to obtain a colorless oil as a 1:1 mixture of diastereoisomers. $^{31}$P NMR (400 MHz, CDCl$_3$): δ 8.39 and 8.11 ppm.

Step 3: 5'-O-[[[(1S)-2-n-butoxy-1-methyl-2-oxoethyl]amino](1-naphthalenyloxy)phosphinyl]-2'-C-methylcytidine

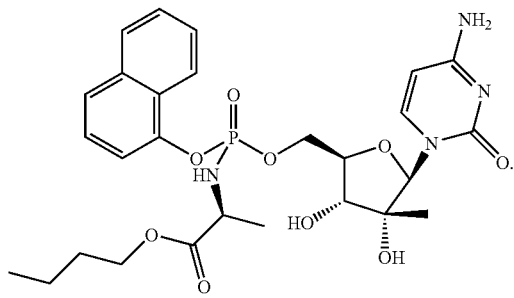

2'-C-Methylcytidine was diluted with THF (0.097 M). The resulting slurry was cooled to −78° C., then tert-butylmagnesium chloride (as 1.0 M solution in THF, 2.2 eq.) was added. The mixture was immediately warmed to 0° C., stirred for thirty min and again cooled to −78° C., then butyl N-[chloro (1-naphthyloxy)phosphoryl]-L-alaninate (as 1.0 M solution in THF, 2.2 eq.) was added dropwise. The reaction was allowed to reach RT overnight, and then was quenched by the addition of water. The aqueous phase was extracted three times with EtOAc, the combined organic phases were washed with brine and dried over Na$_2$SO$_4$. The crude was purified by column chromatography on silica gel (DCM/MeOH gradient from 90:10 to 80:20), and the resulting off white solid was dissolved in DMSO and purified by RP-HPLC. Fractions containing the pure diastereoisomers were combined and freeze-dried to afford the title compounds as their white TFA salts.

First-Eluting Diastereoisomer:
$^1$H NMR (400 MHz, CD$_3$OD) δ 8.24-8.22 (m, 1H), 8.00 (d, J=8.09 Hz, 1H), 7.95-7.93 (m, 1H), 7.76 (d, J=8.09 Hz, 1H), 7.61-7.56 (m, 2H), 7.52 (d, J=7.84 Hz, 1H), 7.48 (t, J=8.08 Hz, 1H), 6.01 (s, 1H), 5.91 (d, J=7.83 Hz, 1H), 4.68 (ddd, J=11.75, 5.05, 1.89 Hz, 1H), 4.57 (ddd, J=11.88, 6.07, 3.28 Hz, 1H), 4.22 (dd, J=9.1, 2.27 Hz, 1H), 4.12-4.03 (m, 3H), 3.84 (d, J=9.1 Hz), 1.63-1.56 (m, 2H), 1.42-1.33 (m, 5H), 1.18 (s, 3H), 0.93 (t, J=7.33 Hz, 3H), NH$_2$, NH, 2×OH not visible, $^{31}$P NMR: (400 MHz, CD$_3$OD) δ: 2.77; MS (ES+) m/z 591 (M+H)$^+$ Second-Eluting Diastereoisomer:
$^1$H NMR (400 MHz, CD$_3$OD): δ 8.28-8.22 (m, 1H), 7.99-7.92 (m, 2H), 7.79 (d, J=8.1 Hz, 1H), 7.65-7.69 (m, 2H), 7.59-7.55 (n, 1H), 7.50 (t, J=8.1 Hz, 1H), 6.00 (s, 1H), 5.86 (d, J=7.83 Hz, 1H), 4.65 (ddd, J=11.7 Hz, J=6.3 Hz, J=1.6 Hz, 1H), 4.53-4.46 (m, 1H), 4.24-4.17 (m, 1H), 4.10-4.00 (m, 3H), 3.83 (d, J=9.3 Hz, 1H), 1.62-1.53 (m, 2H), 1.41-1.32 (m, 5H), 1.17 (s, 3H), 0.93 (t, J=7.4 Hz, 3H); $^{31}$P NMR: (300 MHz, CD$_3$OD) δ: 4.33; MS (ES$^+$) m/z 591 (M+H)$^+$.

EXAMPLE 2

5'-O-[[[(1S)-2-ethoxy-1-methyl-2-oxoethyl]amino](1-naphthalenyloxy)phosphinyl]-2'-C-methylcytidine Step 2: Ethyl N-[chloro(1-naphthyloxy)phosphoryl]-L-alaninate

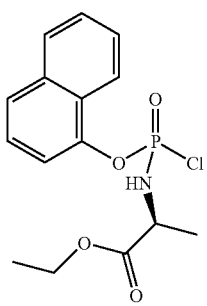

Following the procedure described for Example 1, step 2, treatment of a solution in DCM (0.144 M) of 1-naphthyl dichlorophosphate with L-alanine ethyl ester hydrochloride (1.0 eq.) and Et$_3$N (2.0 eq.) provided the title compound as a colorless oil as a 1:1.1* mixture of diastereoisomers. $^{31}$P NMR (300 MHz, CDCl$_3$) δ: 9.47 and 9.14*.

Step 3: 5'-O-[[[(1S)-2-ethoxy-1-methyl-2-oxoethyl]amino](1-naphthalenyloxy)phosphinyl]-2'-C-methylcytidine

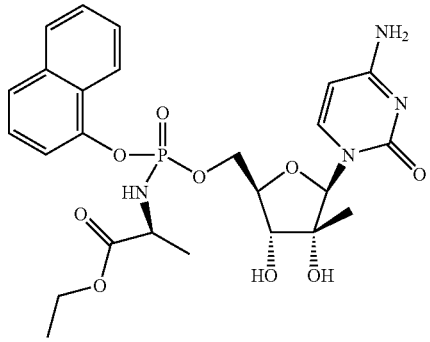

Following the procedure described for Example 1, step 3, 2'-C-methylcytidine in THF (0.097 M) was cooled to −78° C., then tert-butylmagnesium chloride (as 1.0 M solution in THF, 2.2 eq.) was added, followed by the addition of ethyl N-[chloro(1-naphthyloxy)phosphoryl]-L-alaninate (as a 1.0 M solution in THF, 2.2 eq.). The crude product was purified by column chromatography on silica gel (DCM:MeOH=92:8). The resulting solid was dissolved in DMSO and purified by RP-HPLC to afford the title compounds as their white TFA salts.

Second-Eluting Diastereoisomer:
$^1$H NMR (400 MHz, CD$_3$OD): δ 8.27-8.22 (m, 1H), 7.98-7.94 (m, 1H), 7.92 (d, J=7.83 Hz, 1H), 7.79 (d, J=7.83 Hz, 1H), 7.65-7.55 (m, 3H), 7.50 (t, J=7.95 Hz, 1H), 6.01 (s, 1H), 5.85 (d, J=7.83 Hz, 1H), 4.65 (ddd, J=11.81 Hz, J=6.12 Hz, J=1.83 Hz, 1H), 4.49 (ddd, J=11.87 Hz, J=5.81 Hz, J=3.53 Hz, 1H), 4.23-4.17 (m, 1H), 4.11 (q, J=7.07 Hz, 2H), 4.07-3.99 (m, 1H), 3.84 (d, J=9.09 Hz, 1H), 1.36 (dd, J=6.69 Hz, J=0.37 Hz, 3H), 1.22 (t, J=7.07 Hz, 3H), 1.17 (s, 3H); $^{31}$P NMR (400 MHz, CD$_3$OD): δ 4.35; MS (ES$^+$) m/z 563 (M+H)$^+$

EXAMPLE 3

5'-O-[[4-chloro-5-methyl-2-(1-methylethyl)phenoxy][[(1S)-2-ethoxy-1-methyl-2-oxoethyl]amino]phosphinyl]-2'-C-methylcytidine

Step 1: 4-Chloro-2-isopropyl-5-methylphenyl dichlorophosphate

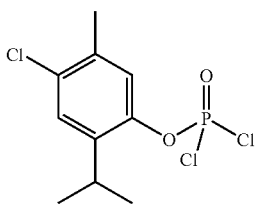

Following the procedure described for Example 1, Step 1, treatment of a solution (0.174 M) in Et$_2$O of 4-chloro-2-isopropyl-5-methyl-phenol with phosphorus oxychloride (1.0 eq.) and Et$_3$N (1.0 eq.) provided the title compound as a colorless oil. $^{31}$P NMR (300 MHz, CD$_3$OD): δ 4.54.

Step 2: Ethyl N-[chloro(4-chloro-2-isopropyl-5-methylphenoxy)phosphoryl]-L-alaninate

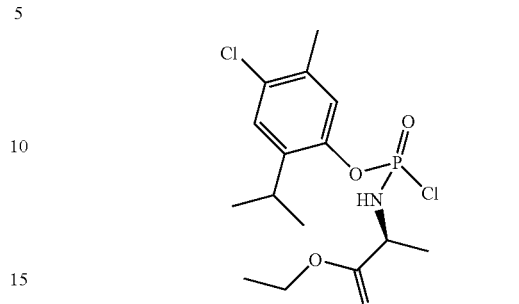

Following the procedure described for Example 1, step 2, treatment of a solution in DCM (0.098 M) of 4-chloro-2-isopropyl-5-methylphenyl dichlorophosphate with L-alanine ethyl ester hydrochloride (1.0 eq.) and Et$_3$N (2.0 eq.) provided the title compound as a colorless oil as a 1:1.35* mixture of diastereoisomers. $^{31}$P NMR (300 MHz, CD$_3$OD): δ 8.5 and 8.8*.

Step 3: 5'-[[4-chloro-5-methyl-2-(1-methylethyl)phenoxy][[(1S)-2-ethoxy-1-methyl-2-oxoethyl]amino]phosphinyl]-2'-C-methylcytidine

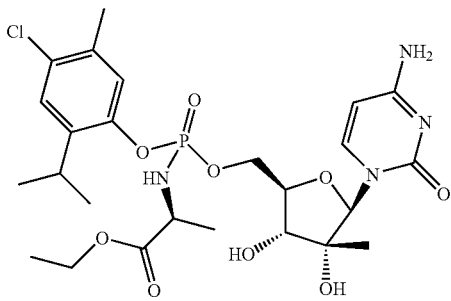

Following the procedure described for Example 1, step 3, 2'-C-methylcytidine in THF (0.097 M) was cooled to −78° C., then tert-butylmagnesium chloride (as 1.0 M solution in THF, 22 eq.) was added, followed by the addition of ethyl N-[chloro(4-chloro-2-isopropyl-5-methylphenoxy)phosphoryl]-L-alaninate (as a 1.0 M solution in THF, 2.2 eq.). The crude product was purified by column chromatography on silica gel (DCM:MeOH gradient from 90:10 to 80:20), the resulting solid was redissolved in DMSO and purified by RP-HPLC to afford the title compounds as their white TFA-salts.

First-Eluting Diastereoisomer:
$^1$H NMR (300 MHz, CD$_3$OD): δ 8.03 (d, J=7.96 Hz, 1H), 7.31 (s, 2H), 6.07 (d, J=7.96 Hz, 1H), 6.01 (s, 1H), 4.61 (ddd, J=11.66, 5.2, 1.54 Hz, 1H), 4.49 (ddd, J=11.72, 5.86, 3.76 Hz, 1H), 4.24-4.16 (m, 3H), 4.01 (dt, J=16.14, 7.3 Hz, 1H), 3.83 (d, J=9.28 Hz, 1H), 2.33 (s, 3H), 1.43 (d, J=7.08 Hz, 3H), 1.31-1.23 (m, 12H), NH$_2$, NH, 2×OH not visible; $^{31}$P NMR: (300 MHz CD$_3$OD): δ 5.03; MS (ES+) m/z 625 and 627 (M+Na$^+$).

Second-Eluting Diastereoisomer:

¹H NMR (300 MHz, CD₃OD) δ 7.96 (d, J=7.83 Hz, 1H), 7.37 (s, 1H), 7.33 (s, 1H), 6.02 (s, 1H), 6.00 (d, J=7.83 Hz, 1H), 4.57 (ddd, J=11.88, 6.45, 1.77 Hz, 1H), 4.41 (ddd, J=11.81, 6.45, 4.04 Hz, 1H), 4.20-4.14 (m, 31-1), 4.00 (dt, J=17.18, 7.33 Hz, 1H), 3.80 (d, J=9.34 Hz, 1H), 2.34 (s, 3H), 1.43 (d, J=7.08 Hz, 3H), 1.29-1.25 (m, 9H), 1.20 (s, 3H), NH₂, NH, 2×OH not visible; ³¹P NMR: (300 MHz, CD₃OD): δ 5.026; MS (ES+) m/z 625 and 627 (M+Na⁺).

EXAMPLE 4

5'-O-[(4-chlorophenoxy)[[(1S)-1-methyl-2-[(9Z)-9-octadecenyloxy]-2-oxoethyl]amino]phosphinyl]-2'-C-methylcytidine Step 2: (9Z)-octadec-9-en-1-yl N-[chloro(4-chlorophenoxy)phosphoryl]-L-alaninate

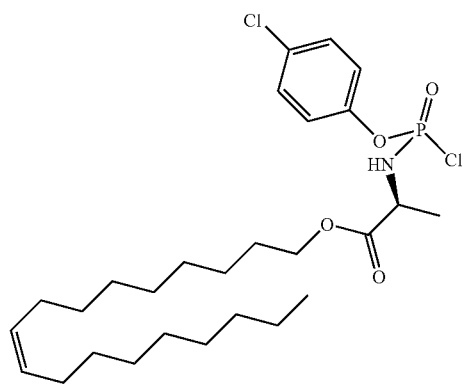

Following the procedure described for Example 1, step 2, treatment of a solution in DCM (0.116 M) of (9Z)-octadec-9-en-1-yl N-[chloro(4-chlorophenoxy)phosphoryl]-L-alaninate with 4-chlorophenyl dichlorophosphate (1.0 eq.) and with Et₃N (2.0 eq.) provided the title compound as a colorless oil as 1.2*:1 mixture of diastereoisomers.

³¹P NMR (400 MHz, CDCl₃): δ 8.31* and 7.97.

Step 3: 5'-O-[(4-chlorophenoxy)[[(1S)-1-methyl-2-[(9Z)-9-octadecenyloxy]-2-oxoethyl]amino]phosphinyl]-2'-C-methylcytidine

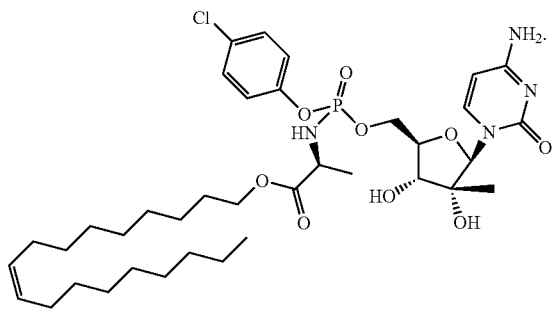

Following the procedure described for Example 1, step 3, 2'-C-methylcytidine in THF (0.097 M) was cooled to −78° C., then tert-butylmagnesium chloride (as 1.0 M solution in THF, 2.2 eq.) was added followed by the addition of (9Z)-octadec-9-en-1-yl N-[chloro(4-chlorophenoxy)phosphoryl]-L-alaninate. The crude mixture was purified by column chromatography on silica gel (DCM:MeOH gradient from 90:10 to 80:20), the resulting solid was redissolved in DMSO and purified by RP-HPLC to afford the title compound as white powders. A 1:1.4* mixture of diastereoisomers at phosphorus was observed by ¹H NMR.

¹H NMR (300 MHz, CD₃OD): δ 8.03 and 8.02* (d, J=7.74 Hz and J*=7.96 Hz, 1H), 7.43-7.39 (m, 2H), 7.32-7.26 (m, 2H), 6.11 and 6.09* (d, J=7.3 Hz and J*=7.52 Hz, 1H), 6.02 and 6.01* (s, 1H), 5.43-5.33 (m, 2H), 4.65-4.54 (m, 1H), 4.51-4.39 (m, 1H), 4.22-4.07 (m, 2H), 4.05-3.95 (m, 1H), 3.83 and 3.82* (d, J=9.07 Hz and J*=9.07 Hz, 1H), 2.07-2.00 (m, 4H), 1.66-1.62 (m, 2H), 1.42-1.33 (m, 26H), 1.22 (s, 3H), 0.94 (t, J=6.2 Hz, 3H), NH₂, NH, 2×OH not visible; ³¹P NMR: (300 MHz, CD₃OD): δ 5.15 and 5.12* (s, 1P). MS (ES+) m/z 769 and 771 (M+H)⁺.

EXAMPLE 5

5'-O-[(4-chlorophenoxy)[[(1S)-2-ethoxy-1-methyl-2-oxoethyl]amino]phosphinyl]-2'-C-methylcytidine Step 2: Ethyl N-[chloro(4-chlorophenoxy)phosphoryl]-L-alaninate

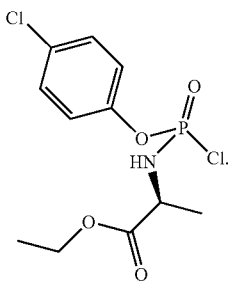

Following the procedure described for Example 1, step 2, treatment of a solution in DCM (0.090 M) of 4-chlorophenyl dichlorophosphate with L-alanine ethyl ester hydrochloride (1.0 eq.) and Et₃N (2.0 eq.) provided the title compound as a colorless oil as a 1:1* mixture of diastereoisomers.

³¹P NMR (300 MHz, CDCl₃): δ 9.43 and 9.11*.

Step 3: 5'-O-[(4-chlorophenoxy)[[(1S)-2-ethoxy-1-methyl-2-oxoethyl]amino]phosphinyl]-2'-C-methylcytidine

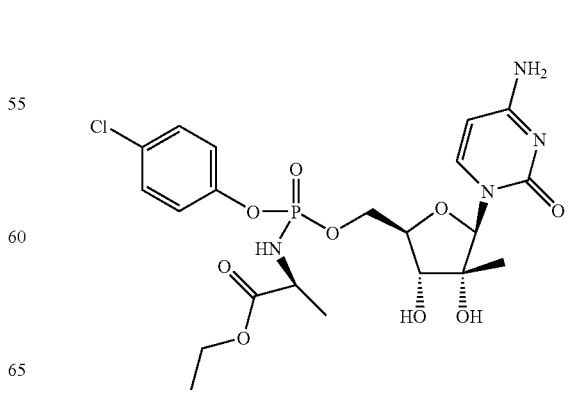

Following the procedure described for Example 1, step 3, 2'-C-methylcytidine in THF (0.097 M) was cooled to −78° C., then tert-butylmagnesium chloride (as 1.0 M solution in THF, 2.2 eq.) was added, followed by the addition of ethyl N-[chloro(4-chlorophenoxy)phosphoryl]-L-alaninate (as a 1.0 M solution in THF, 2.2 eq.). The crude was purified by column chromatography on silica gel (DCM:MeOH=92:8), the resulting solid was redissolved in DMSO and purified by RP-HPLC to afford the title compounds as their white TFA-salts.

Second-Eluting Diastereoisomer:
$^1$H NMR (300 MHz, CD$_3$OD): δ 8.01 (d, J=7.74 Hz, 1H), 7.43 (d, J=8.85 Hz, 2H), 7.31 (d, J=8.85 Hz, 2H), 6.06 (d, J=734 Hz, 1H), 6.02 (s, 1H), 4.58 (ddd, J=11.89 Hz, J=6.25 Hz, J=1.82 Hz, 1H), 4.47-4.38 (m, 1H), 4.24-4.12 (m, 3H), 4.06-3.92 (m, 1H), 3.81 (d, J=9.28 Hz, 1H), 1.41 (d, J=6.85 Hz, 3H), 1.27 (t, J=7.18 Hz, 3H), 1.21 (s, 3H); $^{31}$P NMR (300 MHz, CD$_3$OD): δ 5.10; MS (ES$^+$) m/z 547 (M+H)$^+$

EXAMPLE 6

5'-O-[(4-chlorophenoxy)[[(1S)-1-methyl-2-(1-methylethoxy)-2-oxoethyl]amino]phosphinyl]-2'-C-methylcytidine Step 2: Isopropyl-N-[chloro(4-chlorophenoxy)phosphoryl]-L-alaninate

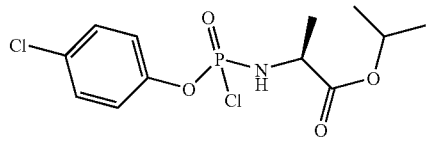

Following the procedure described for Example 1, step 2, the title compound was isolated as a yellow oil and as a mixture of two diastereoisomers at phosphorus.
$^{31}$P NMR (300 MHz, CDCl$_3$): δ 9.61, 9.35.

Step 3: 5'-O-[(4-chlorophenoxy)[[(1S)-1-methyl-2-(1-methylethoxy)-2-oxoethyl]amino]phosphinyl]-2'-C-methylcytidine

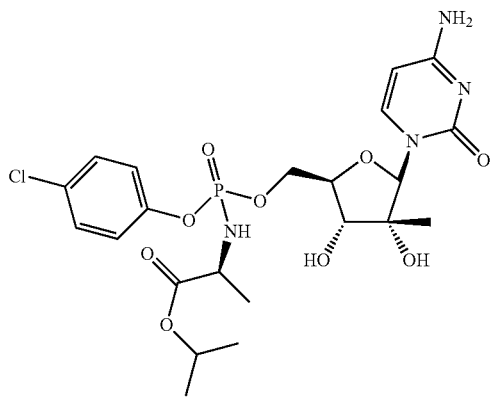

Following the procedure described for Example 1, step 3, the title compound was isolated as a single diastereoisomer at phosphorus and as its TFA salt.

Second-Eluting Diastereoisomer:
$^1$H NMR (300 MHz, CD$_3$OD): δ 8.0 (d, J=7.7 Hz, 1H), 7.41 (d, J=8.7 Hz, 2H), 7.3 (d, J=8.7 Hz, 2H), 6.05 (d, J=7.96 Hz, 1H), 6.0 (s, 1H), 5.02-4.94 (m, 1H), 4.56 (ddd, J=11.7, 6.4, 1.7 Hz, 1H), 4.41 (ddd, J=11.8, 6.35, 3.7 Hz, 1H), 4.21-4.14 (m, 1H), 3.99-3.89 (m, 1H), 3.80 (d, J=9.2 Hz, 1H), 1.39 (d, J=7.1 Hz, 3H), 1.25 (d, J=6.2 Hz, 6H), 1.20 (s, 3H). $^{31}$PNMR (400 MHz, CD$_3$OD): δ 5.13. MS (ES$^+$) m/z 561 (M+H)$^+$.

EXAMPLE 7

5'-O-[[[(1S)-2-n-butoxy-1-methyl-2-oxoethyl]amino](4-chlorophenoxy)phosphinyl]-2'-C-methylcytidine Step 2: n-Butyl N-[chloro(4-chlorophenoxy)phosphoryl]-L-alaninate

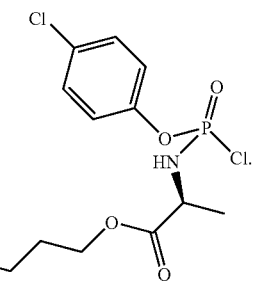

Following the procedure described for Example 1, step 2, treatment of a solution in DCM (0.090 M) of the commercially available 4-chlorophenyl dichlorophosphate with L-alanine ethyl ester hydrochloride (1.0 eq.) and Et$_3$N (2.0 eq.) provided the title compound as a colorless oil as a 1.1:1* mixture of diastereoisomers. $^{31}$P NMR (400 MHz, CDCl$_3$): δ: 9.52 and 9.28*

Step 3: 5'-O-[[[(1S)-2-n-butoxy-1-methyl-2-oxoethyl]amino](4-chlorophenoxy)phosphinyl]-2'-C-methylcytidine

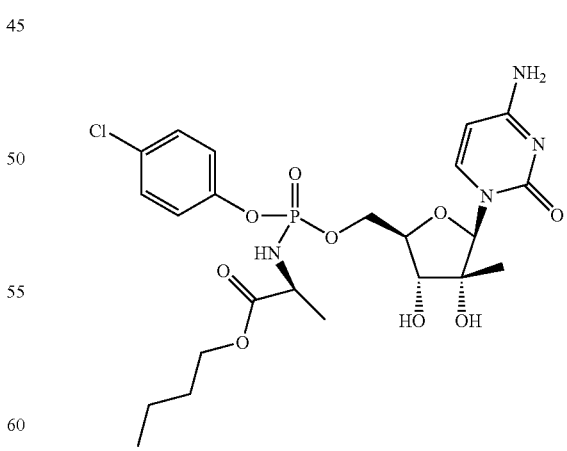

Following the procedure described for Example 1, step 3, 2'-C-methylcytidine in THF (0.097 M) was cooled to −78° C., then tert-butylmagnesium chloride (as 1.0 M solution in THF, 2.2 eq.) was added, followed by the addition of butyl N-[chloro(4-chlorophenoxy)phosphoryl]-L-alaninate (as a 1.0 M solution in THF, 2.2 eq.). The crude was purified by column chromatography on silica gel (DCM:MeOH=92:8), the resulting solid was redissolved in DMSO and purified by RP-HPLC to afford the title compounds as their white TFA-salts.

Second-Eluting Diastereoisomer:
$^1$H NMR (400 MHz, CD$_3$OD): δ 8.01 (d, J=7.83 Hz, 1H), 7.42 (d, J=8.84 Hz, 2H), 731 (d, J=8.08 Hz, 2H), 6.06 (d, J=7.83 Hz, 1H), 6.01 (s, 1H), 4.57 (ddd, J=11.68 Hz, J=6.25 Hz, J=1.71 Hz, 1H), 4.47-4.39 (m, 1H), 4.21-4.06 (m, 3H), 4.05-3.95 (m, 1H), 3.81 (d, J=9.35 Hz, 1H), 1.68-1.58 (m, 2H), 1.49-1.34 (m, 5H), 1.21 (s, 3H), 0.97 (t, J=7.33 Hz, 3H); $^{31}$P NMR (400 MHz, CD$_3$OD): δ 3.97; MS (ES$^+$) m/z 575 (M+H)$^+$

EXAMPLE 8

5'-O-[[(2-n-butoxy-2-oxoethyl)amino](1-naphthalenyloxy)phosphinyl]-2'-C-methylcytidine Step 2: Butyl N-[chloro(1-naphthyloxy)phosphoryl]glycinate

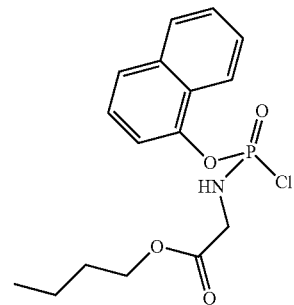

Treatment of a solution in DCM (0.077 M) of 1-naphthyl dichlorophosphate with glycine butyl ester hydrochloride (1.0 eq.) and Et$_3$N (2.0 eq.) provided the title compound as a colorless oil. $^{31}$P NMR (400 MHz, CDCl$_3$): δ 9.28.

Step 3: 5'-O-[[(2-n-butoxy-2-oxoethyl)amino](1-naphthalenyloxy)phosphinyl]-2'-C-methylcytidine

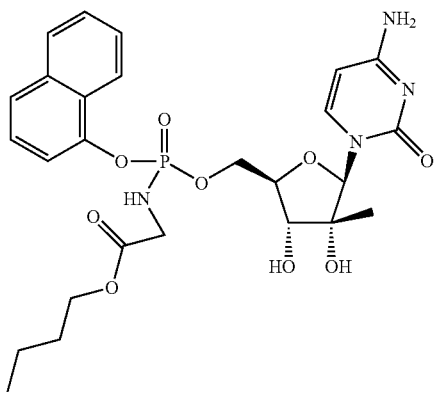

Following the procedure described for Example 1, step 3, 2'-C-methylcytidine in THF (0.097 M) was cooled to −78° C., then tert-butylmagnesium chloride (as 1.0 M solution in THF, 2.2 eq.) was added, followed by the addition of butyl N-[chloro(1-naphthyloxy)phosphoryl]glycinate (as a 1.0 M solution in THF, 2.2 eq.). The crude mixture was purified by column chromatography on silica gel (DCM:MeOH=92:8), the resulting solid was redissolved in DMSO and purified by RP-HPLC to afford the title compound as a diastereoisomeric mixture in the form of a TFA salt.

Mixture of diastereoisomers: $^1$H NMR (400 MHz, CD$_3$OD) δ 8.29-8.20 (m, 1H), 8.02 (d, J=7.83 Hz, 1H), 7.99-7.92 (m, 1H), 7.79 (d, J=8.04 Hz, 1H), 7.67-7.54 (m, 3H), 7.50 (t, J=7.83 Hz, 1H), 5.99 and 5.98*(s, 1H), 5.89 (d, J=7.83 Hz, 1H), 4.69 (ddd, J=11.87 Hz, J=536 Hz, J=1.77 Hz, 1H), 4.57 (ddd, J=11.81 Hz, J=6.12 Hz, J=3.34 Hz, 1H), 4.25-4.18 (m, 1H), 4.12 (t, J=6.44 Hz, 2H), 3.92-3.71 (m, 3H), 1.66-1.56 (m, 2H), 1.45-1.33 (m, 2H), 1.17 (s, 3H), 0.95 (t, J=7.71 Hz, 3H); $^{31}$P NMR (CD$_3$OD) δ 5.79 and 5.44*; MS (ES$^+$) m/z 577 (M+H)$^+$

EXAMPLE 9

5'-O-[[[(1S)-2-(2-ethylbutoxy)-1-methyl-2-oxoethyl]amino]phenoxyphosphinyl]-2'-C-methylcytidine

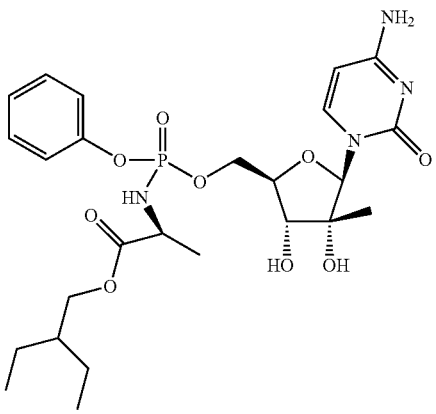

This compound was prepared following the procedure described for Example 1 (starting from phenyl dichlorophosphate and 2-ethylbutyl L-alaninate hydrochloride) and purification by column chromatography on silica gel (DCM:MeOH=92:8) and RP-HPLC (stationary phase: column Phenomenex Luna C$_{18}$(2), 5 μm, 21.2×250 mm, mobile phase: acetonitrile/H$_2$O buffered with NH$_4$HCO$_3$ 5 mM). Fractions containing each of the two pure diastereoisomers were combined and freeze-dried to afford the title compounds as white powders:

First-Eluting Diastereoisomer:
$^1$H NMR (400 MHz, CD$_3$OD): δ 7.73 (d, J=7.5 Hz, 1H), 7.41-7.37 (m, 21-1), 7.28-7.25 (m, 2H), 7.22 (t, J=7.5 Hz, 1H), 6.08 (s, 1H), 5.85 (d, J=7.5 Hz, 1H), 4.58 (ddd, J=11.7, 4.8, 2.0 Hz, 1H), 4.43 (ddd, J=11.7, 5.4, 2.9 Hz, 1H), 4.13-3.95 (m, 4H), 3.75 (d, J=9.2 Hz, 1H), 1.56-1.50 (m, 1H), 1.42-1.35 (m, 7H), 1.10 (s, 3H), 0.91 (t, J=7.4 Hz, 6H); $^{31}$P NMR (400 MHz, CD$_3$OD): δ 3.96; MS (ES$^+$) m/z 569 (M+H)$^+$.

Second-Eluting Diastereoisomer:
$^1$H NMR (400 MHz, CD$_3$OD): δ 7.70 (d, J=7.5 Hz, 1H), 7.41-7.37 (m, 2H), 7.30-7.28 (m, 2H), 7.22 (t, J=7.3 Hz, 1H), 6.06 (s, 1H), 5.85 (d, J=7.5 Hz, 1H), 4.52 (dd, J=10.3, 5.7 Hz, 1H), 4.39 (dd, J=9.5, 5.3 Hz, 1H), 4.12-3.95 (m, 4H), 3.74 (d, J=9.2 Hz, 1H), 1.54-1.48 (m, 1H), 1.39-1.33 (m, 7H), 1.12 (s, 3H), 0.90 (t, J=7.5 Hz, 6H). $^{31}$P NMR (400 MHz, CD$_3$OD): δ 3.79; MS (ES$^+$) m/z 569 (M+H)$^+$.

EXAMPLE 10

5'-O-[[[(1S)-2-(2,2-dimethylpropoxy)-1-methyl-2-oxoethyl]amino]phenoxyphosphinyl]-2'-C-methylcytidine

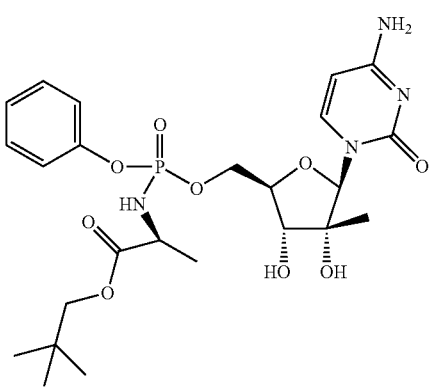

Following the procedure described for Example 1 (starting from phenyl dichlorophosphate and 2,2-dimethylpropyl ester L-alaninate, hydrochloride) and purification by column chromatography on silica gel (DCM/MeOH gradient from 90\10 to 80\20), the resulting solid was redissolved in DMSO and purified by RP-HPLC (stationary phase: column Symmetry C18, 7 μm, 19×300 mm. Mobile phase: acetonitrile/H$_2$O buffered with 0.1% TFA). Fractions containing the pure compounds were combined and freeze-dried to afford the title compound as a white powder as TFA-salt as a 7.1:1* (by NMR) mixture (first eluting:second eluting).

Mixture of diastereoisomers: $^1$H NMR (300 MHz, CD$_3$OD) δ 8.01 and 7.97* (d, J=7.8 Hz and J*=8.1 Hz, 1H), 7.41-7.37 (m, 2H), 7.30-7.20 (m, 3H), 6.03 and 6.00* (d, J=7.8 Hz and J*=7.7 Hz, 1H), 5.99 and 5.98* (s, 1H), 4.60 and 4.56*-4.52* (ddd, J=11.7, 4.8, 2.0 Hz and m*; 1H), 4.45 and 4.42*-4.36* (ddd, J=11.8, 5.8, 3.0 Hz and m*, 1H), 4.18-4.15 (m, 1H), 4.05-3.97 (m, 1H), 3.88-3.78 (m, 3H), 1.40* and 1.37 (d, J*=7.8 Hz and J=7.1 Hz, 3H), 1.22 (br s, 3H), 0.96 and 0.95* (s, 9H), NH$_2$, NH, 2×OH not visible. $^{31}$P NMR: (300 MHz, CD$_3$OD) δ: 5.09 and 4.96*. MS (ES+) m/z 555 (M+H)$^+$.

EXAMPLE 11

Step 3: 5'-O-[[[(1S)-2-(octyloxy)-1-methyl-2-oxoethyl]amino]phenoxyphosphinyl]-2'-C-methylcytidine

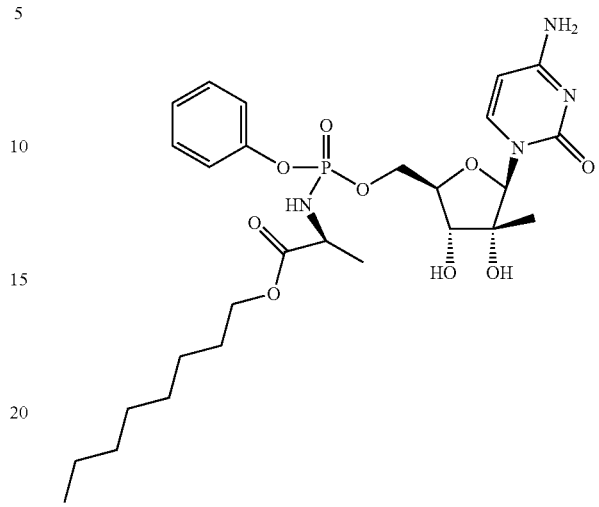

Following the procedures described in Example 1, step 2 (starting from phenyl dichlorophosphate and octyl L-alaninate hydrochloride) and step 3, there was obtained a crude product, which was purified by column chromatography on silica gel (DCM:MeOH=92:8) and purified by RP-HPLC (stationary phase: column Symmetry C$_{18}$, 7 μm, 19×300 mm. Mobile phase: acetonitrile/H$_2$O buffered with 0.1% TFA). Fractions containing the pure compound were combined and freeze-dried to afford the title compound as its TFA salt (white powder; 1:1* of diastereoisomers on phosphorous; first eluting:second eluting*).

Mixture of diastereoisomers: $^1$H NMR (300 MHz, DMSO-d$_6$) δ 9.65 (br s, 1H), 8.72 (br s, 1H), 7.96 and 7.95* (d, J=7.6 Hz and J*=7.9 Hz, 1H), 7.44-7.37 (m, 2H), 7.28-7.20 (m, 3H), 6.20-6.0 (m, 2H), 5.86 and 5.85 (s, 1H), 4.55-4.25 (m, 2H), 4.16-3.97 (m, 3H), 3.95-3.80 (m, 1H), 3.63 (d, 9.2 Hz, 1H), 1.61-1.45 (m, 2H), 1.27 (br s, 3H), 1.07 (s, 3H), 0.91-0.86 (m, 3H). $^{31}$P NMR: (300 MHz, DMSO-d$_6$) δ: 3.82 and 3.67*. MS (ES+) m/z 598 (M+H)$^+$.

EXAMPLE 12

5'-[[[(1S)-1-methyl-2-oxo-2-[(propylpentyl)oxy]ethyl]amino]phenoxyphosphinyl]-2'-C-methylcytidine

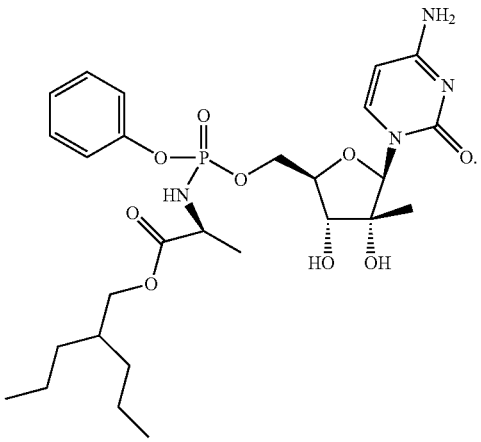

Step 2: L-alanine, N-(chlorophenoxyphosphinyl)-, 2-propylpentyl ester

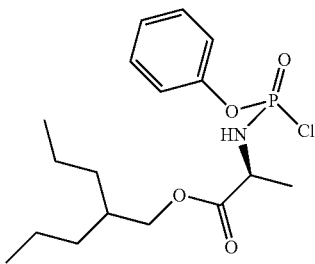

To phenyl dichlorophosphate in DCM (0.086 M) was added (2S)-1-propylpentyloxy-1-oxopropan-2-aminium chloride (1.0 eq.). After cooling to −78° C., neat Et₃N (2.0 eq.) was added and the reaction was left to warm to RT overnight. All volatiles were removed and the resulting white solid was washed with Et₂O and filtered. The filtrate was evaporated in vacuo to afford a colorless oil as a 1:1 mixture of diastereoisomers. ³¹P NMR (400 MHz, CDCl₃): δ 8.22 and 7.93 ppm.

Step 3: 5'-O-[[[(1S)-1-methyl-2-oxo-2-[(propylpentyl)oxy]ethyl]amino]phenoxyphosphinyl]-2'-C-methylcytidine

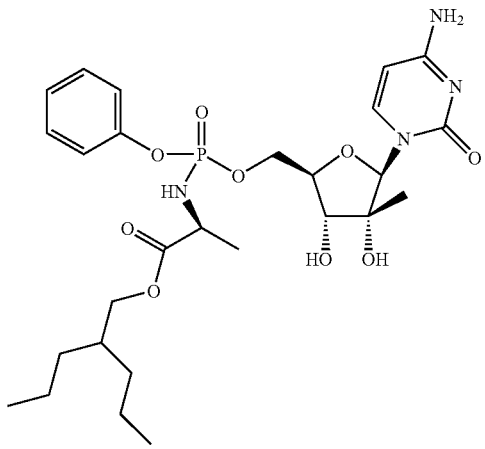

2'-C-Methylcytidine was diluted with THF (0.097 M). The resulting slurry was cooled to −78° C., then tert-butylmagnesium chloride (as 1.0 M solution in THF, 2.2 eq.) was added. The mixture was immediately warmed to 0° C., stirred for 30 min and again cooled to −78° C., then propylpentyl N-[chloro(phenyloxy)phosphoryl]-L-alaninate (as 1.0 M solution in THF, 2.2 eq.) was added dropwise. The reaction was allowed to reach RT overnight, and then was quenched by the addition of water. The aqueous phase was extracted three times with EtOAc, the combined organic phases were dried over Na₂SO₄. The crude product was purified by column chromatography on silica gel (DCM/MeOH 92:8), and the resulting off white solid was dissolved in DMSO and purified by RP-HPLC (stationary phase: column Symmetry C₁₈, 7 μm, 19×300 mm. Mobile phase: acetonitrile/H₂O, water buffered with 5 mM AMBIC). Fractions containing the pure diastereoisomers were combined and freeze-dried to afford the title compounds as a white solid.

First-Eluting Diastereoisomer:
¹H NMR (400 MHz, CD₃OD) δ 7.70 (d, J=7.46 Hz, 1H), 7.45-7.30 (m, 2H), 7.30-7.13 (m, 3H), 6.06 (s, 1H), 5.83 (d, J=7.46 Hz, 1H), 4.63-4.51 (m, 1H), 4.48-4.35 (m, 1H), 4.17-3.87 (m, 4H), 3.73 (d, J=9.1 Hz, 1H), 1.67 (bs, 1H), 1.47-1.17 (m, 11H), 1.08 (s, 3H), 0.89 (bs, 6H). NMR: (400 MHz, CD₃OD) δ: 3.95; MS (ES+) m/z 597 (M+H)⁺

Second-Eluting Diastereoisomer:
¹H NMR (400 MHz, CD₃OD) δ 7.68 (d, J=7.33 Hz, 1H), 7.43-7.32 (m, 2H), 7.31-7.16 (m, 3H), 6.04 (s, 1H), 5.83 (d, J=7.33 Hz, 1H), 4.55-4.45 (m, 1H), 4.42-4.31 (m, 1H), 4.14-3.90 (m, 4H), 3.72 (d, J=9.09 Hz, 1H), 1.72-1.59 (m, 1H), 1.43-1.20 (m, 11H), 1.09 (s, 3H), 0.89 (t, J=6.32 Hz, 6H). ³¹P NMR: (400 MHz, CD₃OD) δ: 3.79; MS (ES+) m/z 597 (M+H)⁺

EXAMPLE 13

5'-O-[[[(1S)-2-[2-(hexyloxy)ethoxy]-1-methyl-2-oxoethyl]amino]phenoxyphosphinyl]-2'-C-methylcytidine

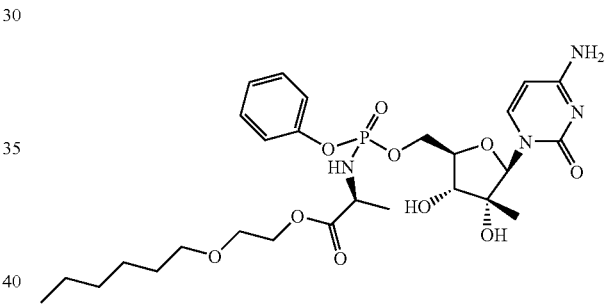

Step 2: 2-(hexyloxy)ethyl N-[chloro(phenoxy)phosphoryl]-L-alaninate

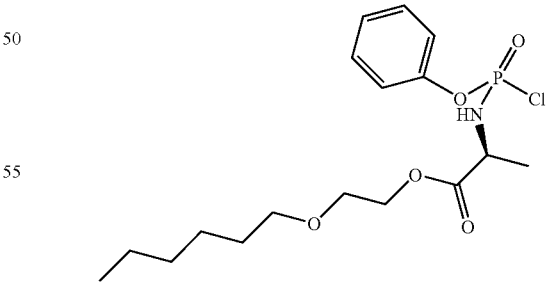

Treatment of a DCM (0.116 M) solution of (2S)-1-[2-(hexyloxy)ethoxy]-1-oxopropan-2-aminium chloride with phenyl dichlorophosphate (1.0 eq.) with triethylamine (2.0 eq.) provided the title compound as a colorless oil as 1:1 mixture of diastereoisomers.

³¹P NMR (400 MHz, CDCl₃, 300 K) δ: 8.03 and 7.67.

Step 3: 5'-O-[[[(1S)-2-[2-(hexyloxy)ethoxy]-1-methyl-2-oxoethyl]amino]phenoxy-phosphinyl]-2'-C-methylcytidine

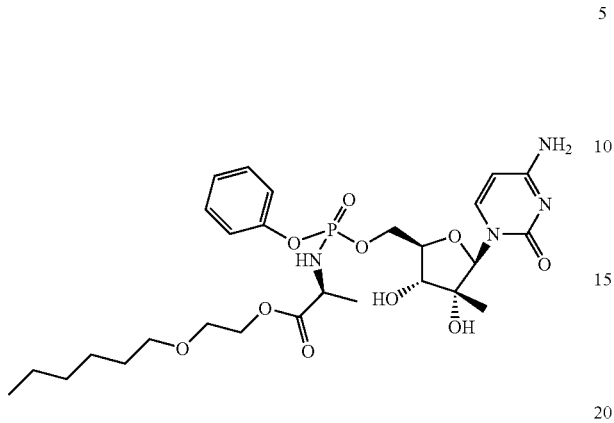

2'-C-Methylcytidine (evaporated twice from toluene) in THF (0.097 M) was cooled to −78° C., tert-butylmagnesium chloride (as 1.0M solution in THF, 2.2 eq.) was added followed by the addition of 2-(hexyloxy)ethyl N-[chloro(phenoxy)phosphoryl]-L-alaninate. The crude product was purified by column chromatography on silica gel (DCM/MeOH gradient from 90/10 to 80/20), the resulting off white solid was dissolved in DMSO and purified by RP-HPLC (stationary phase: column Symmetry C18, 7 μm, 19×300 mm. Mobile phase: acetonitrile/$H_2O$ buffered with 0.1% TFA). Fractions containing the pure compounds were combined and freeze dried to afford the title compounds as a white powder. A 1:1.8* mixture was observed by $^{31}P$ NMR.

$^1H$ NMR (300 MHz, $CD_3OD$) δ: 7.85 and 7.82* (d, J=7.92 Hz and J*=7.92 Hz, 1H), 7.24-7.18 (M, 2H), 7.11-7.02 (m, 3H), 5.87 and 5.83* (d, J=7.83 Hz and J*=7.92 Hz, 1H), 5.81 and 5.80* (s, 1H), 4.45-4.33 (m, 1H), 4.30-4.18 (m, 1H), 4.11-3.94 (m, 3H), 3.87-3.76 (m, 1H), 3.62 and 3.59* (d, J=8.34 Hz and J*=9.30 Hz, 1H), 3.46 (qt, J=4.53 Hz, 2H), 3.28 (t, J=6.60 Hz, 2H), 1.41-1.32 (m, 2H), 1.20-1.13 (m, 9H), 0.99 (s, 3H), 0.74-0.70 (m, 3H). $^{31}P$ NMR: (300 MHz, $CD_3OD$) δ: 3.86 and 3.63* (s, 1P); MS (ES+) m/z 613 $(M+H)^+$

SCHEME 2

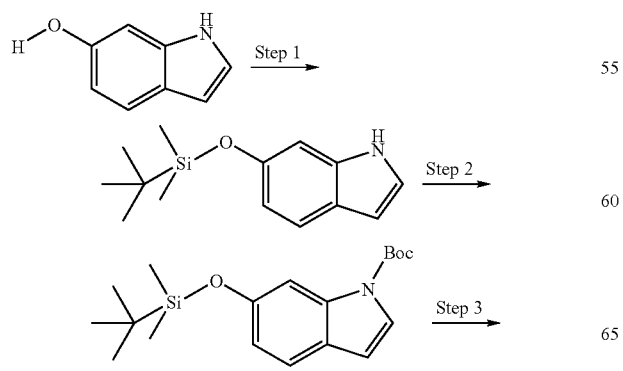

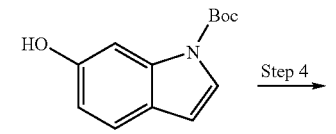

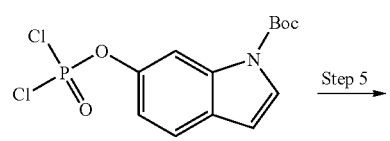

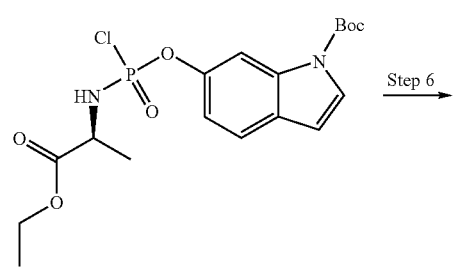

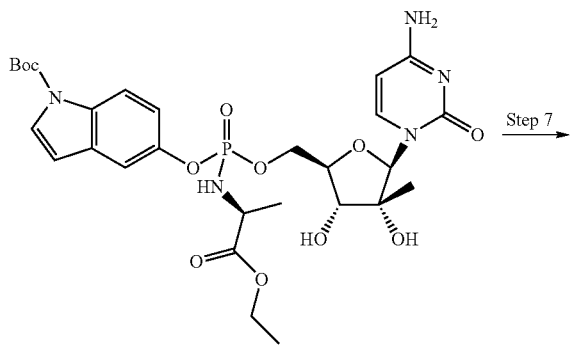

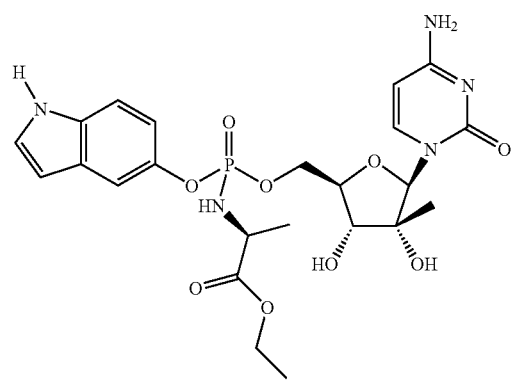

EXAMPLE 14

5'-O-[[[1-[(1,1-dimethylethoxy)carbonyl]-1H-indol-5-yl]oxy][[(1S)-2-ethoxy-1-methyl-2-oxoethyl]amino]phosphinyl]-2'-C-methylcytidine

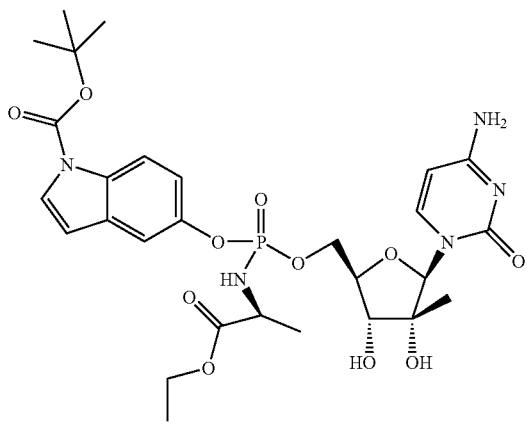

Step 1: 5-{[tert-butyl(dimethyl)silyl]oxy}-1H-indole

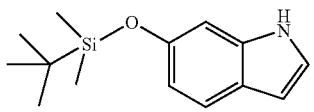

To a stirred solution of 5-hydroxyindole in DCM (0.3 M) was added imidazole (2.0 eq). The mixture was cooled to 0° C. and treated with tert-butyldimethylsilyl chloride (1.0 eq). The resulting mixture was stirred at room temperature for 12 h, diluted with DCM, washed sequentially with H$_2$O, 1N HCl (aq) and finally with brine. The combined organic fractions were dried over Na$_2$SO$_4$. The crude was purified by column chromatography on silica gel (Petroleum ether:Diethyl ether 90/10) to afford the title compound as a white solid.

$^1$H NMR (300 MHz, DMSO-d$_6$) δ 10.92 (br s, 1H), 7.29 (t, J=3.15 Hz, 1H), 7.26 (d, J=8.76 Hz, 1H), 6.96 (d, J=2.25 Hz, 1H), 6.65 (dd, J=2.25 and 8.76 Hz, 1H), 6.34-6.27 (m, 1H), 0.98 (s, 9H), 0.18 (s, 6H).

Step 2: tert-butyl 5-{[tert-butyl(dimethyl)silyl]oxy}-1H-indole-1-carboxylate

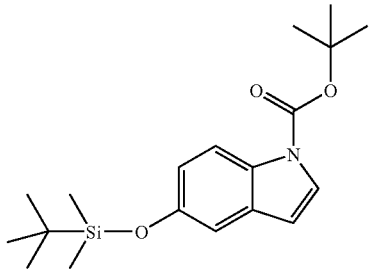

A solution (0.4 M) of 5-{[tert-butyl(dimethyl)silyl]oxy}-1H-indole in DCM was treated at room temperature with DMAP (0.2 eq) and TEA (1.2 eq). Boc$_2$O (1.0 eq) was added and the mixture was stirred for 12 hours at room temperature. The reaction was diluted with DCM, washed with 1N HCl (aq), brine and dried over Na$_2$SO$_4$. The crude was purified by column chromatography on silica gel (Petroleum ether:Diethyl ether 98/2) to afford the title compound as a white solid (50%).

$^1$H NMR (300 MHz, DMSO-d$_6$) δ 7.48 (d, J=8.85 Hz, 1H), 7.64 (d, J=3.60 Hz, 1H), 7.07 (d, J=2.22 Hz, 1H), 6.86 (dd, J=2.22 and 8.85 Hz, 1H), 6.63 (d, J=3.60 Hz, 1H), 1.63 (s, 9H), 0.98 (s, 9H), 0.20 (s, 6H).

Step 3: tert-butyl 5-hydroxy-1H-indole-1-carboxylate

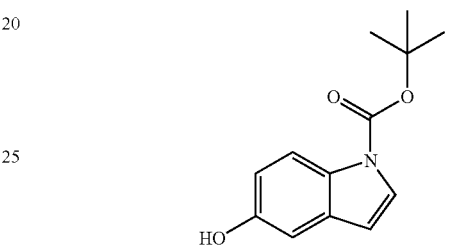

A solution (0.18 M) of tert-butyl 5-{[tert-butyl(dimethyl)silyl]oxy}-1H-indole-1-carboxylate in THF was treated with TBAF (1.1 eq) at 0° C. The mixture was stirred at that temperature for 10 min and allowed to reach room temperature. The reaction was quenched by the addition of saturated aqueous NH$_4$Cl solution and extracted with ethyl acetate. The organic layer was washed with H$_2$O, brine and dried over Na$_2$SO$_4$. The crude product was purified by column chromatography on silica gel (Petroleum ether:EtOAc 92/8) to afford the title compound as a colorless oil.

$^1$H NMR (300 MHz, DMSO-d$_6$) δ 9.20 (s, 1H), 7.87 (d, J=8.85 Hz, 1H), 7.59 (d, J=3.63 Hz, 1H), 6.95 (d, J=2.13 Hz, 1H), 6.81 (dd, J=2.13 and 8.85 Hz, 1H), 6.58 (d, J=3.63 Hz, 1H), 1.65 (s, 9H).

Step 4: 1H-indole-1-carboxylic acid 5-[(dichlorophosphinyl)oxy]-1,1-dimethylethyl ester

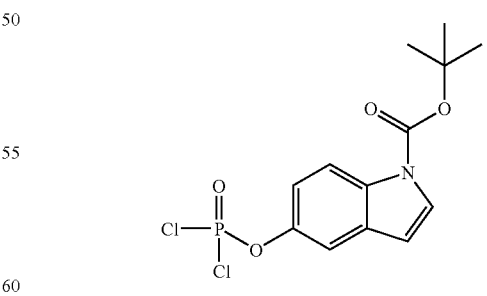

To tert-butyl 5-hydroxy-1H-indole-1-carboxylate in Et$_2$O (0.11 M) was added TEA (1.0 eq.), this solution was cooled to −78° C., then phosphorous oxychloride (1.0 eq) was added neat at that temperature and the resulting solution was left to warm to room temperature overnight. The white slurry was filtered under an inert atmosphere of N$_2$ and all volatiles removed to yield the title compound as a colorless liquid that was used as is for the next step.
$^{31}$P NMR (300 MHz, CDCl3, 300K): δ4.23.

Step 5: 1H-indole-1-carboxylic acid 5-[[chloro [[(1S)-2-ethoxy-1-methyl-2-oxoethyl]amino]phosphinyl]oxy]-1,1-dimethylethyl ester

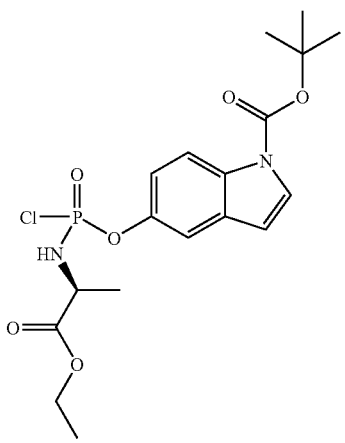

To 1H-indole-1-carboxylic acid 5-[(dichlorophosphinyl)oxy]-1,1-dimethylethyl ester in DCM (0.18 M) was added L-alanine ethyl ester hydrochloride salt (1.0 eq.). Triethylamine (2.0 eq.) was added neat −78° C., and the reaction was left to warm to room temperature overnight. All volatiles were removed and the resulting white solid washed with Et$_2$O. The suspension was filtered and evaporated in vacuo to afford a white solid as a 1:1.04* mixture of diastereoisomers.
$^{31}$P NMR (300 MHz, CDCl$_3$) δ: −8.25* and −8.99.

Step 6: 5'-O-[[[1-[((1,1-dimethylethoxy)carbonyl]-1H-indol-5-yl]oxy][[(1S)-2-ethoxy-1-methyl-2-oxoethyl]amino]phosphinyl]-2'-C-methylcytidine

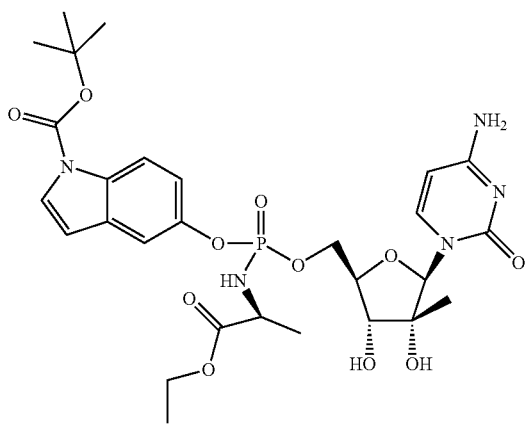

2'-C-methylcytidine (evaporated twice from toluene) was diluted with THF (0.097 M). The resulting slurry was cooled to −78° C., then tert-butylmagnesium chloride (as 1.0M solution in THF, 2.2 eq.) was added. The mixture was immediately warmed to 0° C., stirred for thirty mM and again cooled to −78° C., then 1H-indole-1-carboxylic acid 5-[[chloro [[(1S)-2-ethoxy-1-methyl-2-oxoethyl]amino]phosphinyl]oxy]-1,1-dimethylethyl ester (as 1.0 M solution in THF, 1.6 eq.) was added dropwise. The reaction was allowed to reach room temperature overnight, and quenched by the addition of water. The aqueous phase was extracted three times with EtOAc, the combined organic phases were washed with brine and dried over Na$_2$SO$_4$. The crude was dissolved in DMSO and purified by RP-HPLC (stationary phase: column Phenomenex Luna C18(2) 5 μm, 250×21.20 mm. Mobile phase: acetonitrile/H$_2$O buffered with 5 mM AMBIC). Fractions containing the pure compounds were combined and freeze-dried to afford the title compounds as a white powder.

First-Eluting Diastereoisomer:
$^1$H NMR (300 MHz, DMSO-d$_6$) δ 8.02 (d, J=8.91 Hz, 1H), 7.72 (d, J=3.63 Hz, 1H), 7.56 (d, J=7.45 Hz, 1H), 7.45 (s, 1H), 7.17 (d, J=9.06 Hz, 1H), 7.16 (br s, 1H), 7.10 (br s, 1H), 6.71 (d, J=3.60 Hz, 1H), 6.07 (dd, J=10.17 and 12.66 Hz, 1H), 5.95 (s, 1H), 5.70 (d, J=7.44 Hz, 1H), 5.28 (d, J=6.93 Hz, 1H), 5.08 (s, 1H), 4.47-4.35 (m, 1H), 4.32-4.21 (m, 1H), 4.13-3.96 (m, 3H), 3.89-3.75 (m, 1H), 3.58 (t, J=6.96 Hz, 1H), 1.64 (s, 9H), 1.23 (d, J=6.96 Hz, 3H), 1.13 (t, J=7.05 Hz, 3H), 0.92 (s, 3H); $^{31}$P NMR: 300 MHz, DMSO-d$_6$) δ: 4.05; MS (ES+) m/z 653 (M+H)$^+$ Second-Eluting Diastereoisomer:
$^1$H NMR (300 MHz, DMSO-d$_6$) δ: 8.02 (d, J=8.91 Hz, 1H), 7.72 (d, J=3.63 Hz, 1H), 7.57 (d, J=7.54 Hz, 1H), 7.49 (s, 1H), 7.20 (d, J=7.60 Hz, 1H), 7.18 (br s, 1H), 7.10 (br s, 1H), 6.71 (d, J=3.63 Hz, 1H), 6.00 (dd, J=10.42 and 12.34 Hz, 1H), 5.94 (s, 1H), 5.70 (d, J=7.44 Hz, 1H), 5.23 (d, J=7.05 Hz, 1H), 5.09 (s, 1H), 4.43-4.32 (m, 1H), 4.30-4.18 (m, 1H), 4.13-3.93 (m, 3H), 3.92-3.80 (m, 1H), 3.62 (t, J=7.02 Hz, 1H), 1.65 (s, 9H), 1.25 (d, J=7.02 Hz, 3H), 1.13 (t, J=7.11 Hz, 3H), 0.96 (s, 3H); $^{31}$P NMR (300 MHz, DMSO-d$_6$) δ: 4.16; MS (ES+) m/z 653 (M+H)$^+$

EXAMPLE 15

Step 7: 5'-O-[[[(1S)-2-ethoxy-1-methyl-2-oxoethyl]amino](1H-indol-5-yloxy)phosphinyl]-2'-C-methyl-cytidine

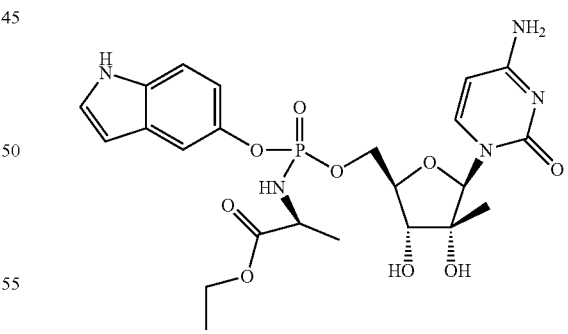

The first eluting 5'-O-[[[1-[(1,1-dimethylethoxy)carbonyl]-1H-indol-5-yl]oxy][[(1S)-2-ethoxy-1-methyl-2-oxoethyl]amino]phosphinyl]-2'-C-methylcytidine from Example 13, Step 6 (0.01 M) in DCM was treated at 0° C. with TFA (0.5 mL) and stirred at RT for 2 h. The reaction was treated with H$_2$O (0.1 mL) and stirred at 35° C. for 2 h. The crude was dissolved in DMSO and purified by RP-HPLC (stationary phase: column Symmetry C18, 7 μm, 19×300 mm. Mobile phase: acetonitrile/H$_2$O buffered with 0.1% TFA). Fractions containing the pure compound were combined and freeze-dried to afford the title compound as a white powder.

$^1$H NMR (300 MHz, DMSO-d$_6$) δ:11.12 (br s, 1H), 8.94 (br s, 1H), 8.12 (br s, 1H), 7.88 (d, J=7.49 Hz, 1H), 7.44-7.31 (m, 3H), 6.95 (d, J=9.64 Hz, 1H), 6.40 (s, 1H), 6.03-5.91 (m, 2H), 5.87 (s, 1H), 5.43 (br s, 1H), 5.30 (br s, 1H), 4.47-4.38 (m, 1H), 4.38-4.22 (m, 1H), 4.14-4.01 (m, 3H), 3.91-3.74 (m, 1H), 3.67-3.58 (m, 1H), 1.22 (d, J=6.99 Hz, 3H), 1.17 (t, J=7.17 Hz, 3H), 1.00 (s, 3H); $^{31}$P NMR (300 MHz, DMSO-d$_6$) δ: 4.27; MS (ES+) m/z 553 (M+H)$^+$.

The additional Examples provided in Tables 1 and 2 were prepared following the procedure depicted in Scheme 1 and described for Examples 1-15 and were obtained either as mixtures of diastereoisomers at the phosphorus stereogenic center or as single diastereoisomers.

TABLE 1

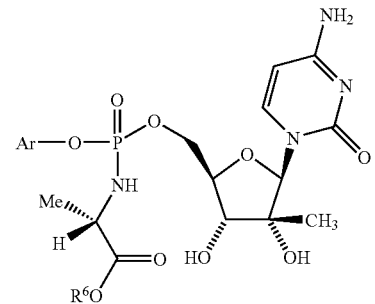

| Ex. | Name | Ar | R$^6$ | MS (M + 1) |
|---|---|---|---|---|
| 16 | 5'-O-[(4-chlorophenoxy)[[(1S)-2-methoxy-1-methyl-2-oxoethyl]amino]phosphinyl]-2'-C-methylcytidine | 4-Cl—Ph | Me | 533 |
| 17 | 5'-O-[[[(1S)-2-methoxy-1-methyl-2-oxoethyl]amino](1-naphthalenyloxy)phosphinyl]-2'-C-methylcytidine | 1-naphthyl | Me | 549 |
| 18 | 5'-O-[[[(1S)-2-ethoxy-1-methyl-2-oxoethyl]amino]phenoxyphosphinyl]-2'-C-methylcytidine | Ph | Et | 513 |
| 19 | 5'-O-[(4-chlorophenoxy)[[(1S)-2-(cyclopropylmethoxy)-1-methyl-2-oxoethyl]amino]phosphinyl]-2'-C-methylcytidine | 4-Cl—Ph | cPr—CH$_2$— | 573 |
| 20 | 5'-O-[[[(1S)-2-methoxy-1-methyl-2-oxoethyl]amino]phenoxyphosphinyl]-2'-C-methylcytidine | Ph | Me | 499 |
| 21 | 5'-O-[[[(1S)-2-methoxy-1-methyl-2-oxoethyl]amino][4-(trifluoromethyl)phenoxy]phosphinyl]-2'-C-methylcytidine | 4-CF$_3$—Ph | Me | 567 |
| 22 | 5'-O-[(4-chlorophenoxy)[[(1S)-1-methyl-2-oxo-2-propoxyethyl]amino]phosphinyl]-2'-C-methylcytidine | 4-Cl—Ph | nPr | 561 |
| 23 | 5'-O-[(4-chlorophenoxy)[[(1S)-1-methyl-2-oxo-2-(tricyclo[3.3.1.1$^{3,7}$]dec-2-yloxy)ethyl]amino]phosphinyl]-2'-C-methylcytidine | 4-Cl—Ph | 2-adamantyl | 653 |
| 24 | 5'-O-[(2-chlorophenoxy)[[(1S)-2-methoxy-1-methyl-2-oxoethyl]amino]phosphinyl]-2'-C-methylcytidine | 2-Cl—Ph | Me | 533 |
| 25 | 5'-O-[(4-bromophenoxy)[[(1S)-2-methoxy-1-methyl-2-oxoethyl]amino]phosphinyl]-2'-C-methylcytidine | 4-Br—Ph | Me | 577 |
| 26 | 5'-O-[[[(1S)-2-methoxy-1-methyl-2-oxoethyl]amino](4-methoxyphenoxy)phosphinyl]-2'-C-methylcytidine | 4-MeO—Ph | Me | 529 |
| 27 | cytidine, 5'-O-[(4-chlorophenoxy)[[(1S)-2-(1,1-dimethylethoxy)-1-methyl-2-oxoethyl]amino]phosphinyl]-2'-C-methyl- | 4-Cl—Ph | tBu | 575 |
| 28 | 5'-O-[(4-chlorophenoxy)[[(1S)-1-methyl-2-oxo-2-(2-propenyloxy)ethyl]amino]phosphinyl]-2'-C-methylcytidine | 4-Cl—Ph | allyl | 559 |
| 29 | 5'-O-[[[(1S)-2-ethoxy-1-methyl-2-oxoethyl]amino][4-(trifluoromethoxy)phenoxy]phosphinyl]-2'-C-methylcytidine | 4-CF$_3$O—Ph | Et | 597 |
| 30 | 5'-O-[[[(1S)-2-ethoxy-1-methyl-2-oxoethyl]amino](2-naphthalenyloxy)phosphinyl]-2'-C-methylcytidine | 2-naphthyl | Et | 563 |
| 31 | 5'-O-[(4-chlorophenoxy)[[(1S)-2-(2,2-difluoroethoxy)-1-methyl-2-oxoethyl]amino]phosphinyl]-2'-C-methylcytidine | 4-Cl—Ph | CHF$_2$CH$_2$— | 583 |
| 32 | 5'-O-[(4-chlorophenoxy)[[(1S)-1-methyl-2-oxo-2-phenoxyethyl]amino]phosphinyl]-2'-C-methylcytidine | 4-Cl—Ph | Ph | 595 |
| 33 | 5'-O-[(4-chlorophenoxy)[[(1S)-1-methyl-2-oxo-2-(phenylmethoxy)ethyl]amino]phosphinyl]-2'-C-methylcytidine | 4-Cl—Ph | Benzyl | 609 |
| 34 | 5'-O-[[[(1S)-2-butoxy-1-methyl-2-oxoethyl]amino](2-chlorophenoxy)phosphinyl]-2'-C-methylcytidine | 2-Cl—Ph | nBu | 575 |

TABLE 1-continued

| Ex. | Name | Ar | R⁶ | MS (M + 1) |
|---|---|---|---|---|
| 35 | 5'-O-[[[(1S)-2-butoxy-1-methyl-2-oxoethyl]amino][(4-chloro-1-naphthalenyl)oxy]phosphinyl]-2'-C-methylcytidine | 4-Cl-1-naphthyl | nBu | 625 |
| 36 | 5'-O-[(4-chlorophenoxy)[[(1S)-2-(cyclohexyloxy)-1-methyl-2-oxoethyl]amino]phosphinyl]-2'-C-methylcytidine | 4-Cl—Ph | nBu | 601 |
| 37 | 5'-O-[(4-chlorophenoxy)[[(1S)-1-methyl-2-(octyloxy)-2-oxoethyl]amino]phosphinyl]-2'-C-methylcytidine | 4-Cl—Ph | nOct | 631 |
| 38 | 5'-O-[(4-chlorophenoxy)[[(1S)-2-(cyclopentyloxy)-1-methyl-2-oxoethyl]amino]phosphinyl]-2'-C-methylcytidine | 4-Cl—Ph | cPen | 587 |
| 39 | 5'-O-[(4-chlorophenoxy)[[(1S)-2-(2-ethylbutoxy)-1-methyl-2-oxoethyl]amino]phosphinyl]-2'-C-methylcytidine | 4-Cl—Ph | 2Et-Bu | 603 |
| 40 | 5'-O-[(4-chlorophenoxy)[[(1S)-1-methyl-2-(1-naphthalenyloxy)-2-oxoethyl]amino]phosphinyl]-2'-C-methylcytidine | 4-Cl—Ph | 1-naphthyl | 645 |
| 41 | 5'-O-[[[(1S)-2-ethoxy-1-methyl-2-oxoethyl]amino][5-methyl-2-(1-methylethyl)phenoxy]phosphinyl]-2'-C-methylcytidine | 2-iPr-5-Me—Ph | Et | 569 |
| 42 | 5'-O-[(4-chlorophenoxy)[[(1S)-1-methyl-2-[(4-methylpentyl)oxy]-2-oxoethyl]amino]phosphinyl]-2'-C-methylcytidine | 4-Cl—Ph | 4-Me-Pen | 603 |
| 43 | 5'-O-[(4-chlorophenoxy)[[(1S)-1-methyl-2-(3-methylbutoxy)-2-oxoethyl]amino]phosphinyl]-2'-C-methylcytidine | 4-Cl—Ph | 3-Me-Bu | 589 |
| 44 | 5'-O-[(4-chlorophenoxy)[[(1S)-2-(heptyloxy)-1-methyl-2-oxoethyl]amino]phosphinyl]-2'-C-methylcytidine | 4-Cl—Ph | nHep | 617 |
| 45 | 5'-O-[(4-chlorophenoxy)[[(1S)-2-(2-methoxyethoxy)-1-methyl-2-oxoethyl]amino]phosphinyl]-2'-C-methylcytidine | 4-Cl—Ph | MeO(CH₂)₂— | 577 |
| 46 | 5'-O-[(4-chlorophenoxy)[[(1S)-2-(3-methoxypropoxy)-1-methyl-2-oxoethyl]amino]phosphinyl]-2'-C-methylcytidine | 4-Cl—Ph | MeO(CH₂)₃— | 591 |
| 47 | 5'-O-[[[(1S)-2-butoxy-1-methyl-2-oxoethyl]amino]phenoxyphosphinyl]-2'-C-methylcytidine | Ph | nBu | 541 |
| 48 | 5'-O-[[[(1S)-2-ethoxy-1-methyl-2-oxoethyl]amino](2-methylphenoxy)phosphinyl]-2'-C-methylcytidine | 2-Me—Ph | Et | 527 |
| 49 | 5'-O-[[[(1S)-2-butoxy-1-methyl-2-oxoethyl]amino][4-chloro-5-methyl-2-(1-methylethyl)phenoxy]phosphinyl]-2'-C-methylcytidine | 4-Cl-2-iPr-5-Me—Ph | nBu | 631 |
| 50 | 5'-O-[[[(1S)-2-(2-ethylbutoxy)-1-methyl-2-oxoethyl]amino]phenoxyphosphinyl]-2'-C-methylcytidine | Ph | 2-Et-Bu | 569 |
| 51 | 5'-O-[[[(1S)-1-methyl-2-[(4-methylpentyl)oxy]-2-oxoethyl]amino]phenoxyphosphinyl]-2'-C-methylcytidine | Ph | 4-Me-Pen | 569 |
| 52 | 5'-O-[[[(1S)-1-methyl-2-(1-methylethoxy)-2-oxoethyl]amino]phenoxyphosphinyl]-2'-C-methylcytidine | Ph | iPr | 527 |
| 53 | 5'-O-[[[(1S)-1-methyl-2-(3-methylbutoxy)-2-oxoethyl]amino]phenoxyphosphinyl]-2'-C-methylcytidine | Ph | 3-Me-Bu | 555 |
| 54 | 5'-O-[[[(1S)-2-(2,2-dimethylpropoxy)-1-methyl-2-oxoethyl]amino]phenoxyphosphinyl]-2'-C-methylcytidine | Ph | neoPen | 555 |

TABLE 1-continued

| Ex. | Name | Ar | R⁶ | MS (M + 1) |
|---|---|---|---|---|
| 55 | 5'-O-[[[(1S)-2-(cyclopentylmethoxy)-1-methyl-2-oxoethyl]amino]phenoxyphosphinyl]-2'-C-methylcytidine | Ph | —CH₂cPen | 567 |
| 56 | 5'-O-[[[(1S)-2-(cyclohexylmethoxy)-1-methyl-2-oxoethyl]amino]phenoxyphosphinyl]-2'-C-methylcytidine | Ph | —CH₂cHex | 581 |
| 57 | 5'-O-[[[(1S)-1-methyl-2-oxo-2-propoxyethyl]amino]phenoxyphosphinyl]-2'-C-methylcytidine | Ph | nPr | 527 |

Abbreviations: nBu = n-butyl; Ph = phenyl; Me = methyl; Et = ethyl; nPr = n-propyl; cPr—CH₂ = cyclopropylmethyl; cPen = cyclopentyl; cHex = cyclohexyl; nOct = n-octyl; 2-Et-Bu = 2-ethylbut-1-yl; 4-Me-Pen = 4-methylpent-1yl; 3-Me-Bu = 3-methylbutyl; nHep = n-heptyl; 2-nPr-Pen = 2-(n-propyl)pent-1-yl.

TABLE 2

| Ex. | Name | Ar | R⁴ | R⁵ | R⁶ | MS (M + 1) |
|---|---|---|---|---|---|---|
| 58 | 5'-O-[(4-chlorophenoxy)[[1-(methoxycarbonyl)cyclopentyl]amino]phosphinyl]-2'-C-methylcytidine | 4-Cl—Ph | cPen | | Me | 573 |
| 59 | 5'-O-[(4-chlorophenoxy)[[(1S)-1-(ethoxycarbonyl)propyl]amino]phosphinyl]-2'-C-methylcytidine | 4-Cl—Ph | Et | H | Et | 561 |
| 60 | 5'-O-[(4-chlorophenoxy)[(2-ethoxy-1,1-dimethyl-2-oxoethyl)amino]phosphinyl]-2'-C-methylcytidine | 4-Cl—Ph | Me | Me | Et | 561 |
| 61 | 5'-O-[(4-chlorophenoxy)[[(1S)-1-(ethoxycarbonyl)-3-methylbutyl]amino]phosphinyl]-2'-C-methylcytidine | 4-Cl—Ph | iPrCH₂ | H | Et | 589 |
| 62 | 5'-O-[(4-chlorophenoxy)[[(1S)-1-(ethoxycarbonyl)pentyl]amino]phosphinyl]-2'-C-methylcytidine | 4-Cl—Ph | nBu | H | Et | 589 |
| 63 | 5'-O-[(4-chlorophenoxy)[(2-methoxy-2-oxoethyl)amino]phosphinyl]-2'-C-methylcytidine | 4-Cl—Ph | H | H | Me | 519 |

TABLE 2-continued

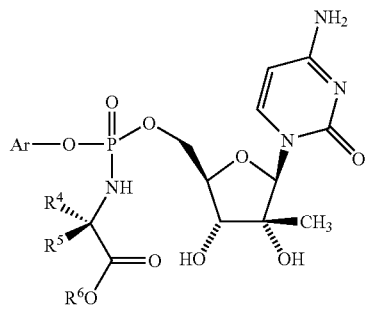

| Ex. | Name | Ar | R⁴ | R⁵ | R⁶ | MS (M + 1) |
|---|---|---|---|---|---|---|
| 64 | 5'-O-[(4-chlorophenoxy)[[(1S)-2-ethoxy-2-oxo-1-phenylethyl]amino]phosphinyl]-2'-C-methylcytidine | 4-Cl—Ph | Ph | H | Et | 609 |
| 65 | 5'-O-[(4-chlorophenoxy)[[(1S)-1-(ethoxycarbonyl)butyl]amino]phosphinyl]-2'-C-methylcytidine | 4-Cl—Ph | nPr | H | Et | 575 |
| 66 | 5'-O-[(4-chlorophenoxy)[[(1S)-1-(ethoxycarbonyl)-3-(methylthio)propyl]amino]phosphinyl]-2'-C-methylcytidine | 4-Cl—Ph | MeS(CH$_2$)$_2$— | H | Et | 662 |
| 67 | 5'-O-[(4-chlorophenoxy)[[(1S)-2-ethoxy-1-(1H-indol-3-ylmethyl)-2-oxoethyl]amino]phosphinyl]-2'-C-methylcytidine | 4-Cl—Ph | 3-indolyl-CH$_2$— | H | Et | 663 |
| 68 | 5'-O-[[[(1S)-2-ethoxy-1-methyl-2-oxoethyl]amino][2-(methoxycarbonyl)phenoxy]phosphinyl]-2'-C-methylcytidine | 2-COOMe—Ph | Me | H | Et | 571 |

Biological Assays:

The assay employed to measure the inhibition of HCV replication is described below.

A. Assay for Inhibition of HCV RNA Replication:

The compounds of the present invention are evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Sub-genomic Hepatitis C Virus RNAs in a Hepatoma Cell Line," *Science* 285: 110 (1999).

Protocol:

The assay is an in situ Ribonuclease protection, Scintillation Proximity based-plate assay (SPA). 10,000-40,000 cells are plated in 100-200 μL of media containing 0.8 mg/mL G418 in 96-well cytostar plates (Amersham). Compounds are added to cells at various concentrations up to 100 μM in 1% DMSO at time 0 to 18 h and then cultured for 24-96 h. Cells are fixed (20 min, 10% formalin), permeabilized (20 min, 0.25% Triton X-100/PBS) and hybridized (overnight, 50° C.) with a single-stranded $^{33}$P RNA probe complementary to the (+) strand NS513 (or other genes) contained in the RNA viral genome. Cells are washed, treated with RNAse, washed, heated to 65° C. and counted in a Top-Count. Inhibition of replication is read as a decrease in counts per minute (cpm).

Human HuH-7 hepatoma cells, which are selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds tested in the replication assay exhibit EC$_{50}$'s less than 100 micromolar.

B. Assay for Intracellular Metabolism:

The compounds of the present invention are also evaluated for their ability to enter a human hepatoma cell line and be converted intracellularly into the corresponding nucleoside 5'-mono-, di-, and triphosphates.

Two cell lines, HuH-7 and HBI10A, are used for intracellular metabolism studies of the compounds of the present invention. HuH-7 is a human hepatoma cell line, and HBI10A denotes a clonal line derived from HuH-7 cells that harbors the HCV bicistronic replicon. HuH-7 cells are plated in complete Dulbecco's modified Eagle's medium containing 10% fetal bovine serum and HBI10A cells in the same containing G418 (0.8 mg/mL) at 1.5×10$^6$ cells/60-mm dish such that cells were 80% confluent at the time of compound addition. Tritiated compound is incubated at 2 μM in the cell medium for 3 or 23 h. Cells are collected, washed with phosphate-buffered saline, and counted. The cells are then extracted in 70% methanol, 20 mM EDTA, 20 mM EGTA, and centrifuged. The lysate is dried, and radiolabeled nucleotides are analyzed using an ion-pair reverse phase (C-18) HPLC on a Waters Millenium system connected to an in-line β-RAM scintillation detector (IN/US Systems). The HPLC mobile phases consists of (a) 10 mM potassium phosphate with 2 mM tetrabutylammonium hydroxide and (b) 50% methanol containing 10 mM potassium phosphate with 2 mM tetrabutylammonium hydroxide. Peak identification is made by comparison of retention times to standards. Activity is expressed as picomoles of nucleotide detected in $10^6$ HuH-7 or HBI10A cells.

The nucleoside aryl phosphoramidates of the present invention are also evaluated for cellular toxicity and anti-viral specificity in the counterscreens described below.

C. Counterscreens:

The ability of the nucleoside aryl phosphoramidates of the present invention to inhibit human DNA polymerases is measured in the following assays.

a. Inhibition of Human DNA Polymerases Alpha and Beta:

Reaction Conditions:
50 µL reaction volume

Reaction Buffer Components:
20 mM Tris-HCl, pH 7.5
200 µg/mL bovine serum albumin
100 mM KCl
2 mM β-mercaptoethanol
10 mM $MgCl_2$
1.6 µM dA, dG, dC, dTTP
$\alpha$-$^{33}$P-dATP Enzyme and Template:
0.05 mg/mL gapped fish sperm DNA template
0.01 U/µL DNA polymerase α or β

Preparation of Gapped Fish Sperm DNA Template:
Add 5 µL 1M $MgCl_2$ to 500 µL activated fish sperm DNA (USB 70076);
Warm to 37° C. and add 30 µL of 65 U/µL of exonuclease III (GibcoBRL 18013-011);
Incubate 5 min at 37° C.;
Terminate reaction by heating to 65° C. for 10 min;
Load 50-100 µL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template is diluted into an appropriate volume of 20 mM Tris-HCl, pH 7.5 and the enzyme is diluted into an appropriate volume of 20 mM Tris-HCl, containing 2 mM (β-mercaptoethanol, and 100 mM KCl. Template and enzyme are pipetted into microcentrifuge tubes or a 96 well plate. Blank reactions excluding enzyme and control reactions excluding test compound are also prepared using enzyme dilution buffer and test compound solvent, respectively. The reaction is initiated with reaction buffer with components as listed above. The reaction is incubated for 1 hour at 37° C. The reaction is quenched by the addition of 20 µL 0.5M EDTA. 50 µL of the quenched reaction is spotted onto Whatman DE81 filter disks and air dried. The filter disks are repeatedly washed with 150 mL 0.3M ammonium formate, pH 8 until 1 mL of wash is <100 cpm. The disks are washed twice with 150 mL absolute ethanol and once with 150 mL anhydrous ether, dried and counted in 5 mL scintillation fluid.

The percentage of inhibition is calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma is measured in reactions that included 0.5 ng/µL enzyme; 10 µM dATP, dGTP, dCTP, and TTP; 2 µCi/reaction [$\alpha$-$^{33}$P]-dATP, and 0.4 µg/µL activated fish sperm DNA (purchased from US Biochemical) in a buffer containing 20 mM Tris pH8, 2 mM β-mercaptoethanol, 50 mM KCl, 10 mM $MgCl_2$, and 0.1 µg/µL BSA. Reactions are allowed to proceed for 1 h at 37° C. and are quenched by addition of 0.5 M EDTA to a final concentration of 142 mM. Product formation is quantified by anion exchange filter binding and scintillation counting. Compounds are tested at up to 50 µM.

The percentage of inhibition is calculated according to the following equation: % inhibition=[1−(cpm in test reaction−cpm in blank)/(cpm in control reaction−cpm in blank)]×100.

The ability of the nucleoside aryl phosphoramidates of the present invention to inhibit HIV infectivity and HIV spread is measured in the following assays:

c. HIV Infectivity Assay

Assays are performed with a variant of HeLa Magi cells expressing both $CXCR^4$ and $CCR^5$ selected for low background β-galactosidase (β-gal) expression. Cells are infected for 48 h, and β-gal production from the integrated HIV-1 LTR promoter is quantified with a chemiluminescent substrate (Galactolight Plus, Tropix, Bedford, Mass.). Inhibitors are titrated (in duplicate) in twofold serial dilutions starting at 100 µm; percent inhibition at each concentration is calculated in relation to the control infection.

d. Inhibition of HIV Spread

The ability of the compounds of the present invention to inhibit the spread of the human immunedeficiency virus (HIV) is measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The nucleoside aryl phosphoramidates of the present invention are also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures are prepared in appropriate media at concentrations of approximately $1.5 \times 10^5$ cells/mL for suspension cultures in 3 day incubations and $5.0 \times 10^4$ cells/mL for adherent cultures in 3 day incubations. 99 µL of cell culture are transferred to wells of a 96-well tissue culture treated plate, and 1 µL of 100-times final concentration of the test compound in DMSO is added. The plates are incubated at 37° C. and 5% $CO_2$ for a specified period of time. After the incubation period, 20 µL of CellTiter 96 Aqueous One Solution Cell Proliferation Assay reagent (MTS) (Promega) is added to each well and the plates are incubated at 37° C. and 5% $CO_2$ for an additional period of time up to 3 h. The plates are agitated to mix well and absorbance at 490 nm is read using a plate reader. A standard curve of suspension culture cells is prepared with known cell numbers just prior to the addition of MTS reagent. Metabolically active cells reduce MTS to formazan. Formazan absorbs at 490 nm. The absorbance at 490 nm in the presence of compound is compared to absorbance in cells without any compound added.

REFERENCE

Cory, A. H. et al., "Use of an aqueous soluble tetrazolium/formazan assay for cell growth assays in culture," *Cancer Commun.* 3: 207 (1991).

The following assays are employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797-801 (1971).

Viruses:

Rhinovirus type 2 (RV-2), strain HGP, is used with KB cells and media (0.1% NaHCO$_3$, no antibiotics) as stated in the Sidwell and Huffman reference. The virus, obtained from the ATCC, is from a throat swab of an adult male with a mild acute febrile upper respiratory illness.

Rhinovirus type 9 (RV-9), strain 211, and rhinovirus type 14 (RV-14), strain Tow, are also obtained from the American Type Culture Collection (ATCC) in Rockville, Md. RV-9 is from human throat washings and RV-14 is from a throat swab of a young adult with upper respiratory illness. Both of these viruses are used with HeLa Ohio-1 cells (Dr. Fred Hayden, Univ. of VA) which are human cervical epitheloid carcinoma cells. MEM (Eagle's minimum essential medium) with 5% Fetal Bovine serum (FBS) and 0.1% NaHCO$_3$ is used as the growth medium.

Antiviral test medium for all three virus types was MEM with 5% FBS, 0.1% NaHCO$_3$, 50 µg gentamicin/mL, and 10 mM MgCl$_2$.

2000 µg/mL is the highest concentration used to assay the compounds of the present invention. Virus was added to the assay plate approximately 5 min after the test compound. Proper controls are also run. Assay plates are incubated with humidified air and 5% CO$_2$ at 37° C. Cytotoxicity is monitored in the control cells microscopically for morphologic changes. Regression analysis of the virus CPE data and the toxicity control data gives the ED50 (50% effective dose) and CC50 (50% cytotoxic concentration). The selectivity index (SI) is calculated by the formula: SI=CC50÷ED50.

b. Determination of In Vitro Antiviral Activity of Compounds Against Dengue, Banzi, and Yellow Fever (CPE Inhibition Assay)

Assay details are provided in the Sidwell and Huffman reference above.

Viruses:

Dengue virus type 2, New Guinea strain, is obtained from the Center for Disease Control. Two lines of African green monkey kidney cells are used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, are obtained from ATCC. Vero cells are used with both of these viruses and for assay.

Cells and Media:

MA-104 cells (BioWhittaker, Inc., Walkersville, Md.) and Vero cells (ATCC) are used in Medium 199 with 5% FBS and 0.1% NaHCO$_3$ and without antibiotics.

Assay medium for dengue, yellow fever, and Banzi viruses is MEM, 2% FBS, 0.18% NaHCO$_3$ and 50 µg gentamicin/mL.

Antiviral testing of the compounds of the present invention is performed according to the Sidwell and Huffman reference and similar to the above rhinovirus antiviral testing. Adequate cytopathic effect (CPE) readings are achieved after 5-6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, is obtained from the Center for Disease Control. Vero cells are grown and used as described above. Test medium is MEM, 1% FBS, 0.1% NaHCO$_3$ and 50 µg gentamicin/mL.

Antiviral testing of the compounds of the present invention is performed following the methods of Sidwell and Huffman which are similar to those used to assay for rhinovirus activity. Adequate cytopathic effect (CPE) readings are achieved after 5-6 days.

d. Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method is used which is described in "Microtiter Assay for Interferon: Microspectrophotometric Quantitation of Cytopathic Effect," *Appl. Environ. Microbiol.* 31: 35-38 (1976). A Model EL309 microplate reader (Bio-Tek Instruments Inc.) is used to read the assay plate. ED$_{50}$'s and CD$_{50}$'s are calculated as above.

Example of a Pharmaceutical Formulation

As a specific embodiment of an oral composition of a compound of the present invention, 50 mg of the compound of Example 1 or Example 2 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of the structural formula I:

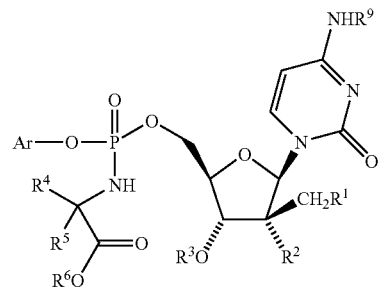

or a pharmaceutically acceptable salts thereof; wherein n is 0, 1, or 2;

Ar is phenyl, naphthyl, pyridinyl, pyrimidinyl, pyrazinyl, pyridazinyl, indolyl, quinolinyl, or isoquinolinyl, wherein Ar is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^1$ is hydrogen or fluoro;

$R^2$ is fluoro, methoxy, or $OR^{10}$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

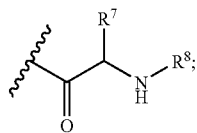

$R^{10}$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

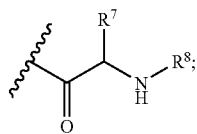

or $R^3$ and $R^{10}$ together with the oxygen atoms to which they are attached form a five-membered cyclic carbonate;

$R^4$ is hydrogen, $C_{1-5}$ alkyl, phenyl, or benzyl;

wherein alkyl is optionally substituted with one substituent selected from the group consisting of fluorine, hydroxy, methoxy, amino, carboxy, carbamoyl, guanidino, mercapto, methylthio, 1H-imidazolyl, and 1H-indol-3-yl; and wherein phenyl and benzyl are optionally substituted with one to two substituents independently selected from the group consisting of halogen, hydroxy, and methoxy;

$R^5$ is hydrogen or methyl;

or $R^4$ and $R^5$ together with the carbon atom to which they attached form a 3- to 6-membered aliphatic spirocyclic ring system;

$R^6$ is hydrogen, $C_{1-16}$ alkyl, $C_{2-20}$ alkenyl, $(CH_2)_nC_{3-6}$ cycloalkyl, phenyl, benzyl, or adamantyl;

wherein alkyl, alkenyl, cycloalkyl, and adamantyl are optionally substituted with one to three substituents independently selected from halogen, hydroxy, carboxy, $C_{1-4}$ alkoxy;

and wherein phenyl and benzyl are optionally substituted with one to three substituents independently selected from halogen, hydroxy, cyano, $C_{1-4}$ alkoxy, trifluoromethyl, and trifluoromethoxy;

$R^7$ is hydrogen, $C_{1-5}$ alkyl, or phenyl $C_{0-2}$ alkyl;

$R^8$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl; and $R^9$ is hydrogen, $C_{1-8}$ alkylcarbonyl, or $C_{1-8}$ alkyloxycarbonyl.

2. The compound of claim 1 wherein $R^1$ is hydrogen or fluoro, $R^2$ is hydroxy, and $R^3$ is hydrogen.

3. The compound of claim 1 wherein $R^1$ is hydrogen or fluoro, $R^2$ is fluoro, and $R^3$ is hydrogen.

4. The compound of claim 1 wherein Ar is phenyl optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl.

5. The compound of claim 4 wherein Ar is phenyl substituted with three to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl.

6. The compound of claim 5 wherein Ar is phenyl substituted with three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl.

7. The compound of claim 1 wherein Ar is indolyl.

8. The compound of claim 1 wherein $R^5$ is hydrogen and $R^4$ is selected from the group consisting of hydrogen, methyl, ethyl, n-propyl, isopropyl, isobutyl, 2-methyl-1-propyl, hydroxymethyl, fluoromethyl, mercaptomethyl, carboxymethyl, carbamoylmethyl, 1-hydroxyethyl, 2-carboxyethyl, 2-carbamoylethyl, 2-methylthioethyl, 4-amino-1-butyl, 3-amino-1-propyl, 3-guanidino-1-propyl, 1H-imidazol-4-ylmethyl, phenyl, benzyl, 4-hydroxybenzyl, and 1H-indol-3-ylmethyl.

9. The compound of claim 8 wherein $R^4$ is methyl or benzyl.

10. The compound of claim 9 wherein $R^4$ is methyl.

11. The compound of claim 1 wherein $R^6$ is $C_{7-16}$ alkyl.

12. The compound of claim 11 wherein $R^6$ is $C_{8-12}$ alkyl.

13. The compound of claim 12 wherein $R^6$ is $C_8$ alkyl.

14. The compound of claim 1 wherein Ar is phenyl or indolyl each of which is optionally substituted with one to three substituents selected from halogen and $C_{1-4}$ alkyl; $R^4$ is methyl; $R^6$ is ethyl or butyl; and $R^5$ is hydrogen.

15. The compound of claim 1 wherein Ar is unsubstituted phenyl and $R^6$ is $C_8$ alkyl.

16. The compound of claim 1 which is selected from the group consisting of:

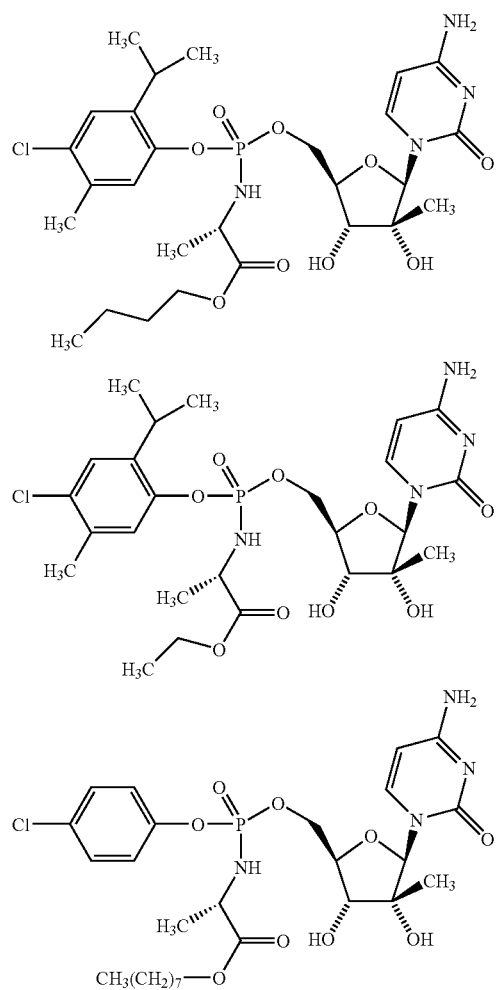
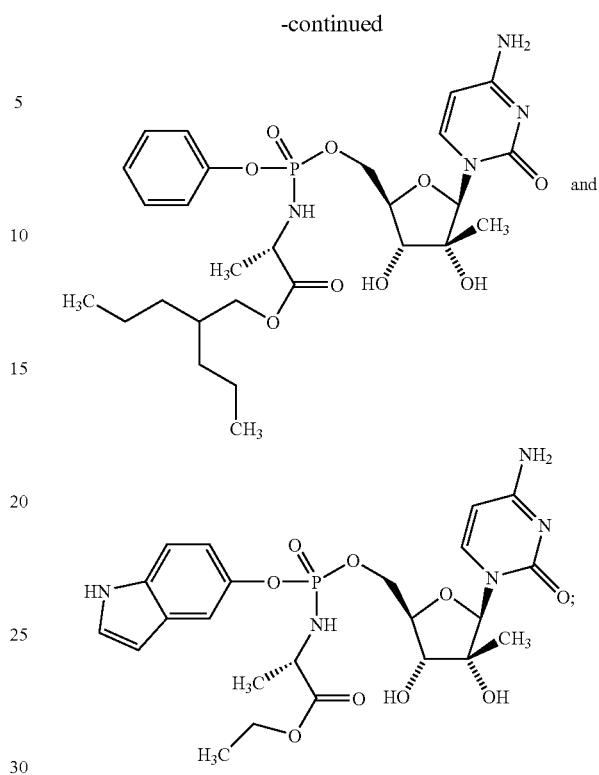

or a pharmaceutically acceptable salt thereof.

17. A pharmaceutical composition comprising a compound of claim 1 and a pharmaceutically acceptable carrier.

18. A method for treating hepatitis C virus infection in a mammal, which comprises administering to the mammal a therapeutically effective amount of a compound of claim 1, or a pharmaceutically acceptable salt thereof.

* * * * *